(12) United States Patent
Kono et al.

(10) Patent No.: US 10,288,867 B2
(45) Date of Patent: May 14, 2019

(54) DRIVING UNIT, OPTICAL UNIT, IMAGING APPARATUS, AND ENDOSCOPE

(71) Applicant: OLYMPUS CORPORATION, Tokyo (JP)

(72) Inventors: Shinya Kono, Tokyo (JP); Takehiko Iguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 164 days.

(21) Appl. No.: 15/181,576

(22) Filed: Jun. 14, 2016

(65) Prior Publication Data
US 2016/0282601 A1    Sep. 29, 2016

Related U.S. Application Data

(63) Continuation of application No. PCT/JP2014/072900, filed on Sep. 1, 2014.

(30) Foreign Application Priority Data

Dec. 16, 2013  (JP) ................................. 2013-259138

(51) Int. Cl.
*A61B 1/00* (2006.01)
*A61B 1/05* (2006.01)
(Continued)

(52) U.S. Cl.
CPC ........ *G02B 23/243* (2013.01); *A61B 1/00096* (2013.01); *A61B 1/00188* (2013.01);
(Continued)

(58) Field of Classification Search
CPC ...... G02B 7/08; H02K 41/354; H02K 41/356; A61B 1/00096; A61B 1/00188; A61B 1/05
(Continued)

(56) References Cited

U.S. PATENT DOCUMENTS 4,488,039 A * 12/1984 Sato .................... A61B 1/00188
250/201.2
2004/0207745 A1    10/2004 Tsuruta et al.
(Continued)

FOREIGN PATENT DOCUMENTS

CN          1538234 A     10/2004
CN        201107446 Y      8/2008
(Continued)

OTHER PUBLICATIONS

International Search Report dated Dec. 2, 2014 issued in PCT/JP2014/072900.

*Primary Examiner* — Aaron B Fairchild
(74) *Attorney, Agent, or Firm* — Scully, Scott, Murphy & Presser, P.C.

(57) ABSTRACT

The drive unit includes a tubular fixed part, a tubular movable part, and a voice coil motor. The tubular fixed part is with a given axis as center, a tubular movable part 3 is located inside of the fixed part and having the axis as center, and a voice coil motor is capable of moving the movable part relatively with respect to the fixed part in the axial direction by a coil located in the fixed part and a magnet located in the movable part. In a state where the magnet is placed in the movable part, a first distance from the axis to the diametrically outer surface of the magnet is longer than a second distance from the axis to the inner circumference surface of the fixed part.

8 Claims, 25 Drawing Sheets

(51) Int. Cl.
   *G02B 7/08*   (2006.01)
   *G02B 7/10*   (2006.01)
   *G02B 23/24*  (2006.01)
   *H04N 5/225*  (2006.01)

(52) U.S. Cl.
   CPC ............... *A61B 1/05* (2013.01); *G02B 7/08* (2013.01); *G02B 7/102* (2013.01); *G02B 23/2438* (2013.01); *G02B 23/2484* (2013.01); *H04N 2005/2255* (2013.01)

(58) Field of Classification Search
   USPC .......................................... 310/12.16, 12.26
   See application file for complete search history.

(56) References Cited

U.S. PATENT DOCUMENTS

| | | |
|---|---|---|
| 2008/0285162 A1 | 11/2008 | Fujita |
| 2009/0086335 A1 | 4/2009 | Tsuruta et al. |

FOREIGN PATENT DOCUMENTS

| | | | |
|---|---|---|---|
| CN | 101533146 A | | 9/2009 |
| JP | H02-301023 A | | 12/1990 |
| JP | H 02301023 A | * | 12/1990 |
| JP | H06-189518 A | | 7/1994 |
| JP | H10-150759 A | | 6/1998 |
| JP | H 10150759 A | * | 6/1998 |
| JP | 2006-227062 A | | 8/2006 |
| JP | 2006227062 A | * | 8/2006 |
| JP | 2006-276565 A | | 10/2006 |

* cited by examiner (b)

DRIVING UNIT, OPTICAL UNIT, IMAGING APPARATUS, AND ENDOSCOPE

CROSS-REFERENCE TO RELATED APPLICATIONS

This application is a continuation claiming priority on the basis of Japan Patent Application No. 2013-259138 applied in Japan on Dec. 16, 2013 and based on PCT/JP2014/072900 filed on Sep. 1, 2014. The contents of both the PCT application and the Japan Application are incorporated herein by reference.

BACKGROUND OF THE INVENTION AND RELATED ART STATEMENT

The present invention relates to a drive unit, an optical unit, an imaging apparatus, and an endoscope, in which a voice coil motor is used to drive a movable part for advanceable/retractable movement.

An imaging apparatus such as a digital camera includes a drive unit for axial movement of a lens unit including lenses and a lens frame for holding the lenses in place. The drive unit is mounted on a guide member such as a lens barrel in such a way as to be movable in the optical axis direction, and the lens unit is axially moved by a driving source such as a motor for focal length adjustment, focusing, etc. A voice coil motor (VCM) is used as that driving source. The voice coil motor includes a coil and a permanent magnet, and there is an electromagnetic force generated by electric current flowing through the coil and a magnetic field created by the permanent magnet. The generated electromagnetic force allows for axial movement of the lens unit. To boost up the electromagnetic force and efficiently transmit it to the lens unit, a plurality of coils and a plurality of permanent magnets are occasionally used (see Patent Publications JP(A) 02-301023 and JP(A) 06-189518).

SUMMARY OF THE INVENTION

According to a certain aspect of the invention, there is a drive unit provided, which includes:
a tubular fixed part with a given axis as center,
a tubular movable part located inside of the fixed part and having the axis as center, and
a voice coil motor capable of moving the movable part relatively with respect to the fixed part in the axial direction by a coil located in the fixed part and a magnet located in the movable part, wherein: in a state where the magnet is placed in the movable part, a first distance from the axis to a diametrically outer surface of the magnet is longer than a second distance from the axis to an inner circumference surface of the fixed part.

DETAILED DESCRIPTION OF EMBODIMENTS

The drive unit according to the embodiment described herein is now explained.

Figure 1:
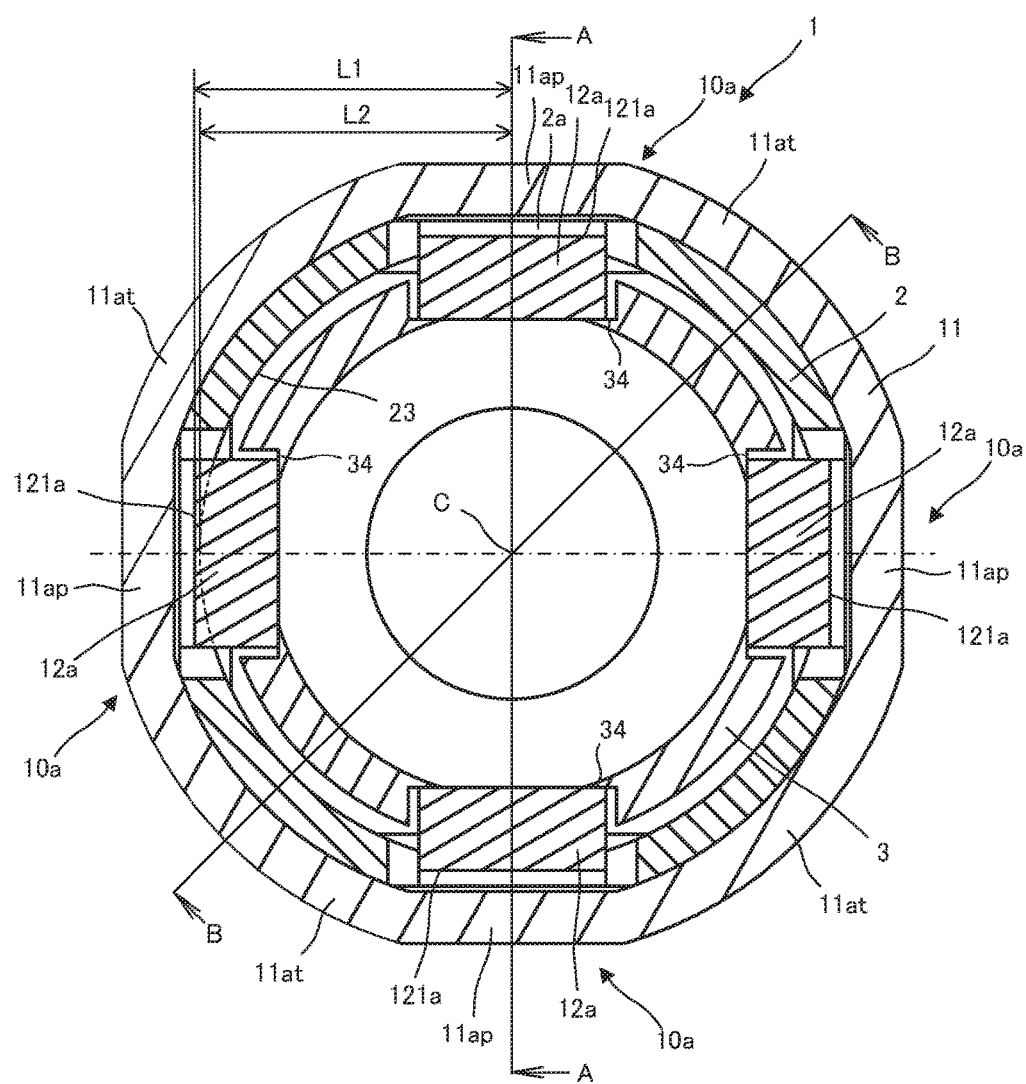
FIG. 1 is illustrative of the drive unit according to the first embodiment of the invention.
Figure 2A:
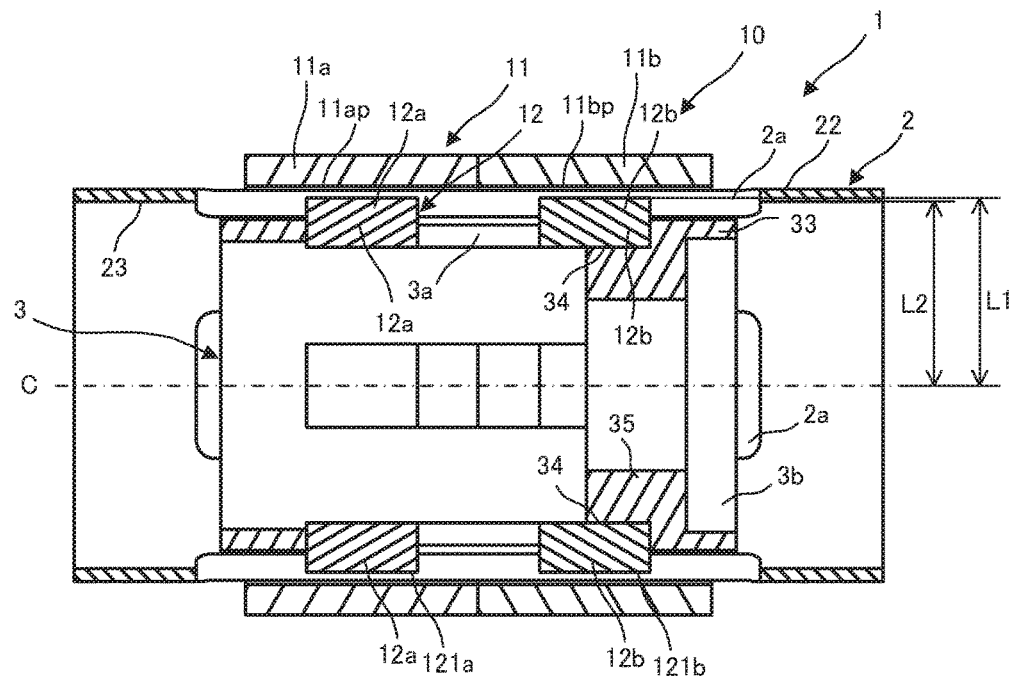
FIGS. 2A and 2B are sectional views of the drive unit according to the first embodiment.
Figure 2B:
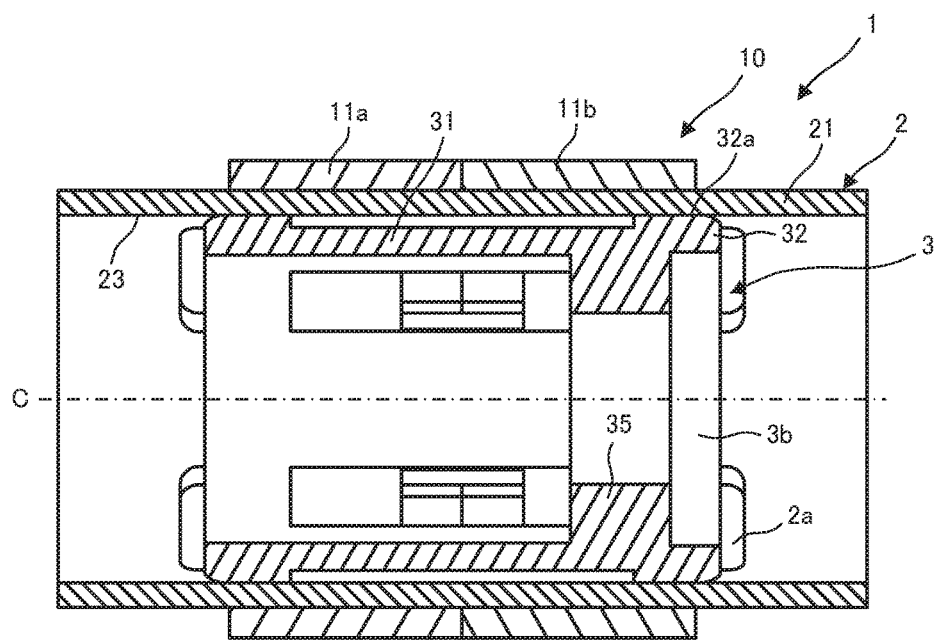
Figure 3:
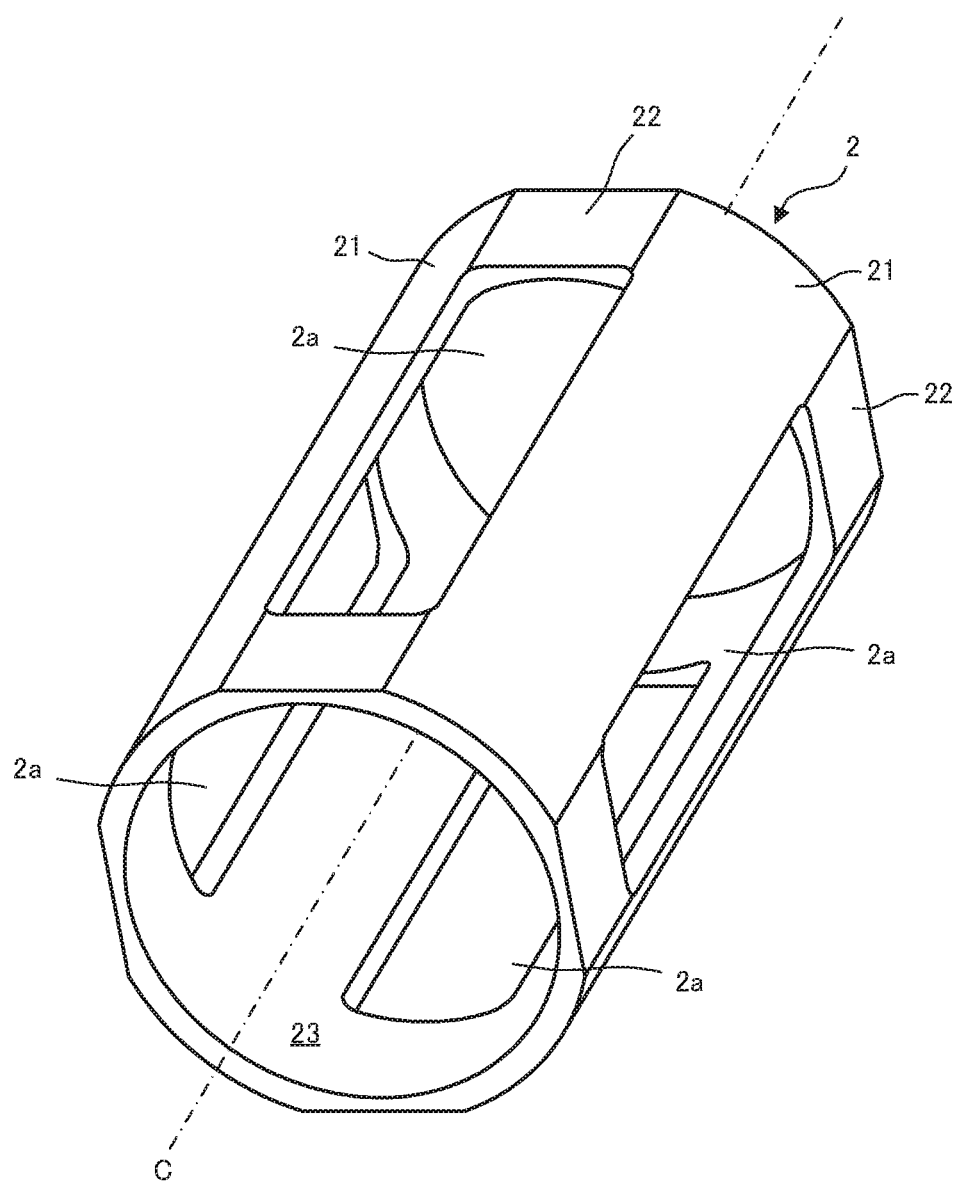
FIG. 3 is illustrative of the fixed part of the drive unit according to the first embodiment.
Figure 4:
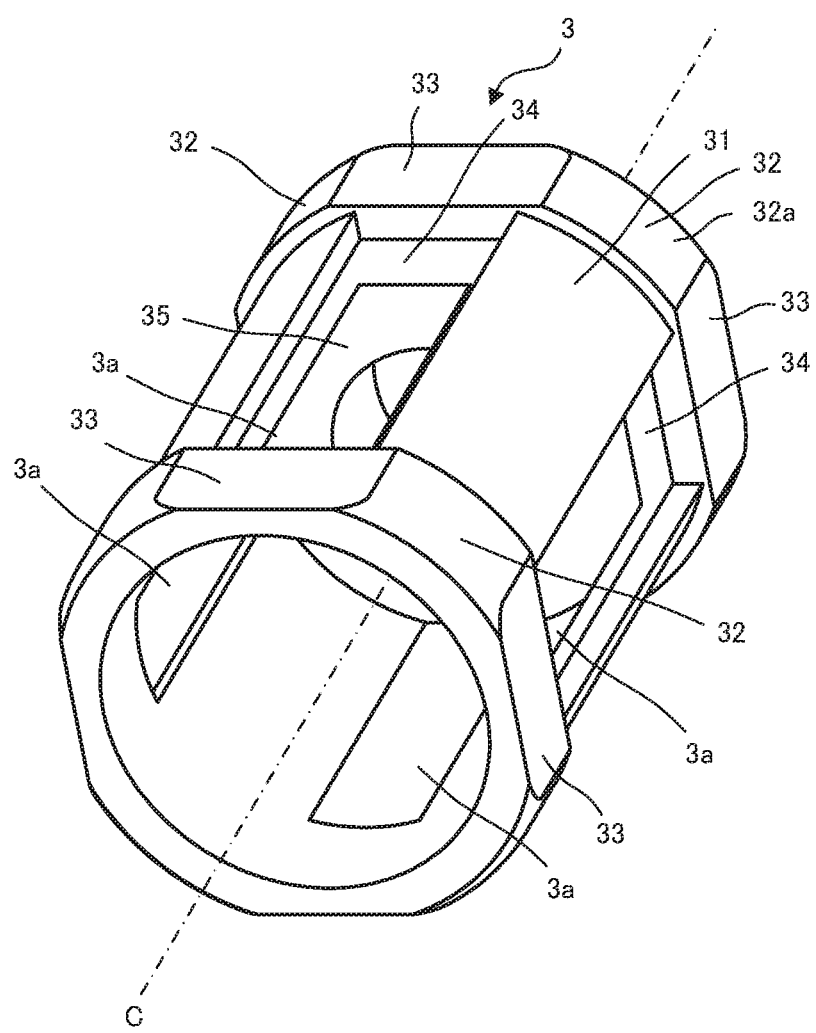
FIG. 4 is illustrative of the movable part of the drive unit according to the first embodiment.

FIG. 1 is a sectional view of the drive unit according to the first embodiment of the invention. FIGS. 2A and 2B are sectional view of the drive unit according to the first embodiment: FIG. 2A is a sectional view of FIG. 1 as taken on section A-A and FIG. 2B is a sectional view of FIG. 1 as taken on section B-B. FIG. 3 is illustrative of the fixed part of the drive unit according to the first embodiment, and FIG. 4 is illustrative of the movable part of the drive unit according to the first embodiment. Note here that the sectional view of FIG. 1 is taken along a position where the first voice coil motor 10a is located.

As shown in FIGS. 2A and 2B, the drive unit 1 according to the embodiment described herein includes a fixed part 2, a movable part 3 movable relative to the fixed part 2, and a voice coil motor 10 capable of generating driving force for moving the movable part 3 relative to the fixed part 2.

As shown in FIG. 3, the fixed part 2 is a member having a tubular form with respect to a given axis C. The fixed part 2 according to the first embodiment includes a tubular portion 21 and a planar portion 22 formed on a part of the outer circumference side of the tubular portion 21. Note here that the inner circumference side of the planar portion 22 may be in a cylindrical shape. A part of the planar portion 22 is lightened as indicated by 2a. In the first embodiment described herein, there are four diametrically orthogonal planar portions 22 provided for each 90° with the axis C of the tubular portion 21 as center. Each planar portion 22 includes a lightened site in the form of an opening 2a in a position except both its axial ends. Note here that the opening 2a may be formed in at least a part of the planar portion 22 or, alternatively, it may protrude out of a part of the tubular portion 21.

As shown in FIG. 4, the movable part 3 is a member having a tubular form with respect to the given axis C. The movable part 3 according to the first embodiment includes a tubular portion 31, protruding edges 32 formed at both ends of the tubular portion 31 in the axis C direction of the tubular portion 31 and having an outer diameter larger than the diameter of the tubular portion 31, a planar portion 33 formed on a part of the outer circumference side of the protruding edge 32, a step portion 34 formed between the planar portions 33 at both the ends in the direction of the axis C and nearer to the inner circumference side of the tubular portion 31, and a small inner-diameter portion 35 formed on one side of the axial direction and having an inner diameter smaller than the diameter of the inner circumference surface of the tubular portion 31. The tubular portion 31 and protruding edge 32 of the movable part 3 may be assembled of separate members.

A part of the step portion 34 is formed with an opening 3a. The outer end face of the small inner-diameter portion 35 in the axis C direction is provided with a recess 3b. In the first embodiment described herein, there are four step portions 34 provided for each 90° with the axis C of the tubular portion 31 as center, and a part of each step portion 34 is provided with an opening 3a. The step portions 34 form four diametrically orthogonal planes for each 90° with respect to the center of the axis C.

As shown in FIGS. 2A and 2B, the voice coil motor 10 includes a coil 11 located on the fixed part 2 and a magnet 12 located on the movable part 3 in such a way as to be opposite to the coil 11.

As shown in FIG. 2A, the coil 11 in the first embodiment includes a first coil 11a wound around the outer circumference of the fixed part 2 and a second coil 11b aligning parallel to the first coil 11a in the axis C direction and wound around the outer circumference of the fixed part 2. Referring to the first coil 11a and the second coil 11b adjacent to each other in the axis C direction, it is preferable that the leads are wound in the opposite directions for series connection. The first coil 11a and the second coil 11b include planes 11ap and 11bp, respectively, corresponding to the openings 2a in the fixed part 2. That is, in the first coil 11a and the second coil 11b, the planes 11ap and 11bp and the cylindrical portions 11at and 11bt are alternately arranged in the circumferential direction.

Referring to the magnet 12 shown in FIG. 2A, a first magnet 12a and a second magnet 12b are axially arranged in the step portion 34 in the movable part 3 for each 90° with respect to the center of the axis such that they are opposite to the planes 11p of the first coil 11a and the second coil 11b. This ensures that the first magnet 12a and the second magnet 12b are stably held so that there is a stable magnetic field created so as to prevent shakes of the movable part 3 that moves relative to the fixed part 2.

It is preferable that the first magnet 12a and the second magnet 12b adjacent to each other in the axial direction are magnetized in the diametrical direction such that the magnetic poles are mutually in the opposite directions. For instance, the first coil 11a side of the first magnet 12a may be magnetized as the S-pole and the other side may be magnetized as the N-pole, the second coil 11b side of the second magnet 12b may be magnetized as the N-pole and the other side may be magnetized as the S-pole.

In the drive unit 1 according to the first embodiment, the movable part 3 having the first magnet 12a and the second magnet 12b in opposition to the first coil 11a and the second coil 11b, respectively, is located on the inner circumference side of the fixed part 2 having the first coil 11a and the second coil 11b wound around. Accordingly, the planes 11ap and 11bp of the first coil 11a and the second coil 11b are each present in a magnetic field in the direction orthogonal to the diametrically outer surfaces 121a and 121b of the first magnet 12a and the second magnet 12b. It is thus possible to improve on driving efficiency and provide rapid movement of the movable part 3. As the diametrically outer surfaces 121a and 121b of the first magnet 12a and the second magnet 12b are formed of planes, it makes the assembling of the drive unit 1 easier.

Preferably, the sum of the axial widths of the first coil 11a and the second coil 11b is greater than the axial width of the first magnet 12a and the second magnet 12b such that throughout the range of movement of the movable part 3, the first magnet 12a and the second magnet 12b are each always placed in the axial width of the first coil 11a and the second coil 11b.

In a state where the first magnet 12a and the second magnet 12b are placed or mounted on the movable part 3, the diametrically outer surfaces 121a and 121b of the first magnet 12a and the second magnet 12b are located in the openings 2a in the fixed part 2 as shown in FIGS. 1 and 2. In other words, the first distance L1 from the axis C to the diametrically outer surfaces 121a and 121b of the first magnet 12a and the second magnet 12b, respectively, is longer than the second distance L2 from the axis C to the inner circumference surface 23 of the fixed part 2. As the first distance L1 gets longer than the second distance L2, the diameter of the fixed part 2 can be smaller and, hence, the size and weight of the drive unit 1 can be smaller. This ensures that the driving efficiency of the drive unit 1 is boosted up enough to provide rapid movement of the movable part 3.

As shown in FIG. 2B, the outer circumference surface of the protruding edge 32 in the movable part 3 forms a sliding surface 32a in contact with the inner circumference surface 23 of the fixed part 2. Contact of the inner circumference surface 23 of the fixed part 2 with the sliding surface 32a of the movable part 3 allows for movement of the movable part 3 while it comes in constant contact with the fixed part 2. In turn, this prevents tilting of the movable part 3 relative to the fixed part 2, making sure unerring movement of the movable part 3.

Further, it is preferable that the drive unit 1 is formed symmetrically with respect to the axis C. The structure allowing for contact of the inner circumference surface 23 of the fixed part 2 with the sliding surface 32a of the movable part 3 is combined with the symmetrical configuration of the whole drive unit 1 with respect to the axis C so that the center of gravity can be positioned on the axis C, contributing to further prevention of tilting of the movable part 3 relative to the fixed part 2.

While the magnets 12 are located for each 90° with the axis C as center in the first embodiment, it is to be understood that they may also be located at any desired angles other than 90°.

Figure 5A:
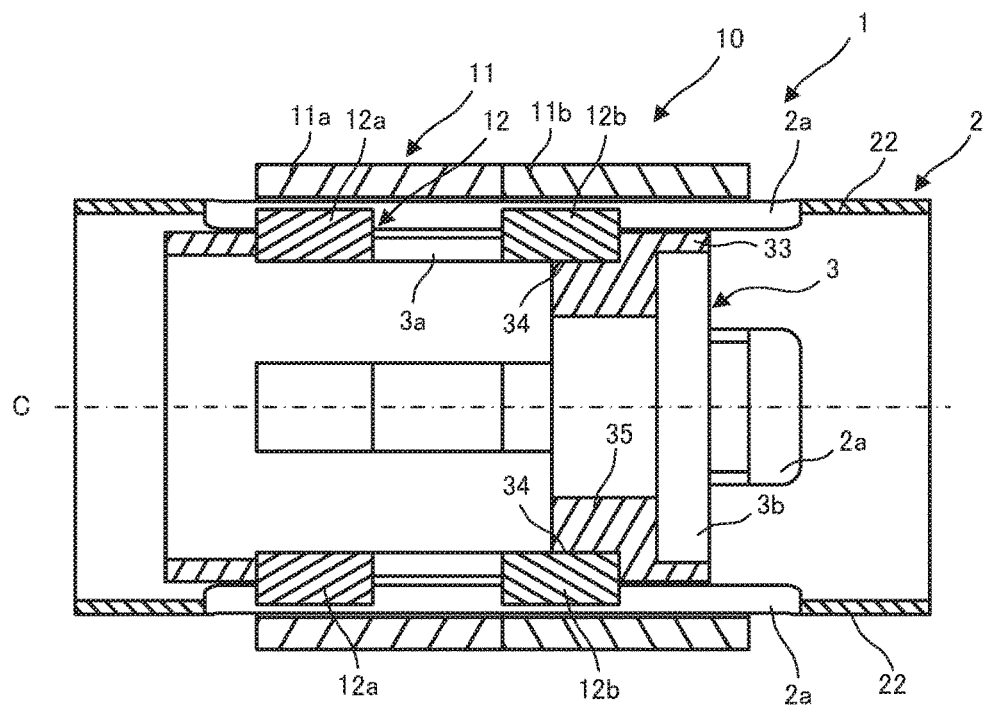
FIGS. 5A and 5B are illustrative of one actuation state of the drive unit according to the first embodiment.
Figure 5B:
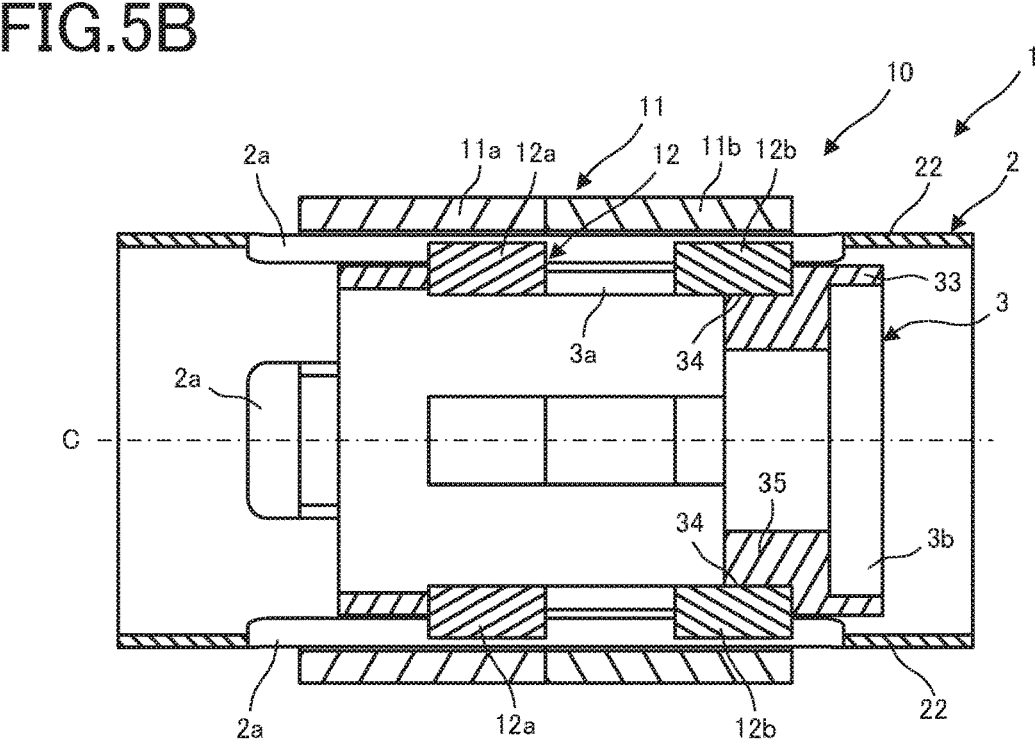

FIGS. 5A and 5B are illustrative of the actuation state of the drive unit according to the first embodiment: FIG. 5A shows that the movable part 3 is moving left on the sheet plane, and FIG. 5B shows that the movable part 3 is moving right on the sheet plane.

Upon the passage of electric current through the drive unit 1 having such structure, an axial force is generated in the movable part 3 under the influence of a magnetic field of the magnet 12 with the result that the movable part 3 moves in the axis C direction relative to the fixed part 2. For instance, if electric current through the first coil 11a and second coil 11b is controlled, the movable part 3 can then move from the position indicated in FIG. 5A to the position indicated in FIG. 5B relative to the fixed part 2. Note here that even while the movable part 3 is moving, the diametrically outer surface of the magnet 12 is located within the opening 2a in the fixed part 2.

Thus, the drive unit 1 according to the embodiment described herein can be reduced in terms of size and weight, and boosted-up driving efficiency allows for rapid movement of the movable part 3. Even during actuation, the inner circumference surface 23 of the fixed part 2 comes into contact with the sliding surface 32a of the movable part 3 so that tilting of the movable part 3 relative to the fixed part 2 can be held back for unerring movement of the movable part 3.

Figure 6A:
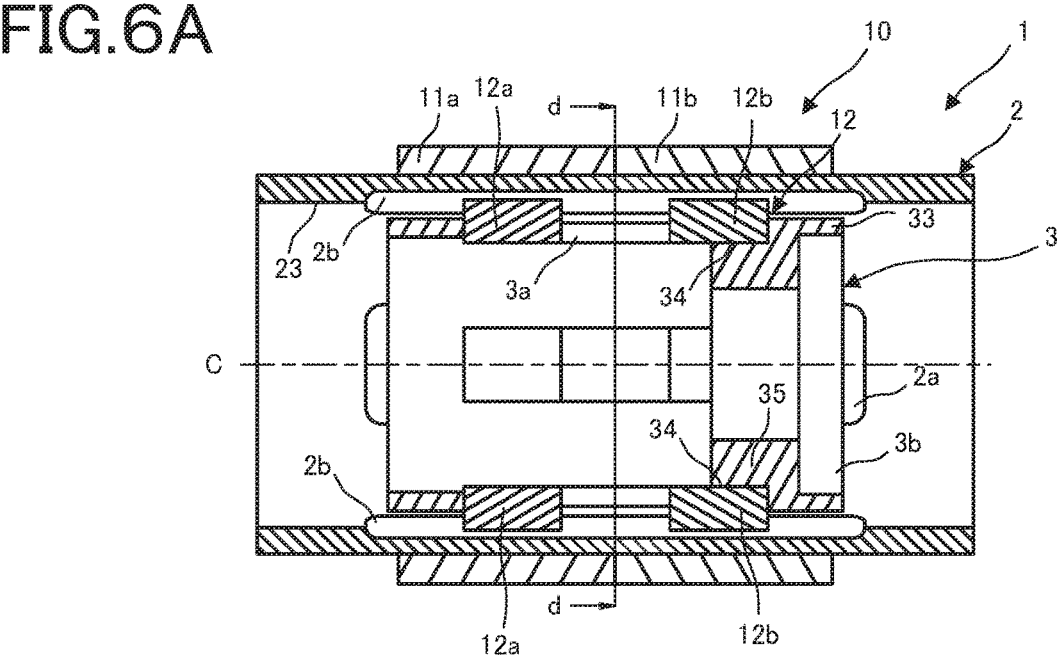
FIGS. 6A and 6B are illustrative of the drive unit according to the second embodiment of the invention.
Figure 6B:
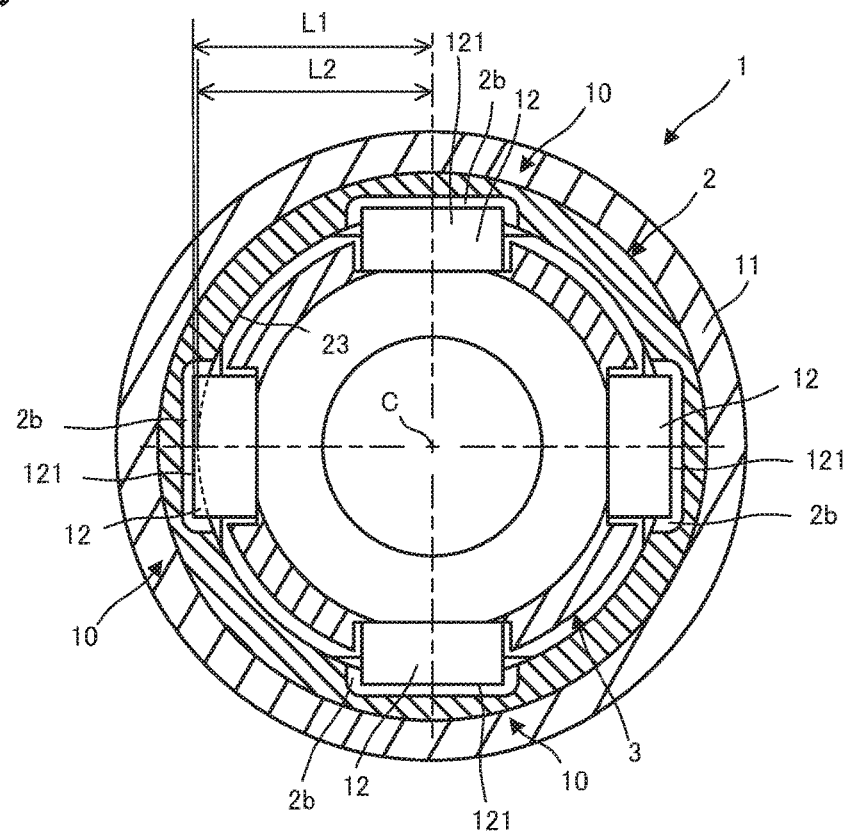

FIGS. 6A and 6B are illustrative of the drive unit according to the second embodiment of the invention: FIG. 6A is a sectional view in the axial direction, and FIG. 6B is a sectional view of FIG. 6A as taken on section d-d. Note here that in what follows, when there is no need for marking the first coil 11a off from the second coil 11b, both will be described all together as the coil 11, and when there is no need for making the first magnet 12a off from the second magnet 12b, both will be described all together as the magnet 12.

The drive unit 1 according to the second embodiment has a structure where a recess 2b is used in place of the opening 2a formed in the fixed part 2 according to the first embodiment.

In the drive unit 1 according to the second embodiment, the fixed part 2 is a member having a tubular form, as shown in FIG. 6. In the fixed part 2 according to the second embodiment, a part of the inner circumference surface 23 of the tubular portion 21 is provided with a recess 2b working as a lightened site. In the second embodiment, there are four recesses 2b provided in the inner circumference surface 23 of the tubular portion 21 for each 90° with the axis C as center. The shape of the recess 2b should preferably conform well to the shape of the diametrically outer surface 121 of the magnet 12.

In a state where the magnet 12 is placed in the movable part 3, a part of the magnet 12 is located in the recess 2b in the fixed part 2, as shown in FIG. 6. In other words, the first distance L1 from the axis C to the diametrically outer surface 121 of the magnet 12 is longer than the second distance L2 from the axis C to the inner circumference surface 23 of the fixed part 2. As the first distance L1 gets longer than the second distance L2, the diameter of the fixed part 2 can be smaller and, hence, the size and weight of the drive unit 1 can be smaller. This ensures that the driving efficiency the drive unit 1 is boosted up enough to provide rapid movement of the movable part 3.

As compared with the opening 2a in the fixed part 2 according to the first embodiment, the formation of the recess 2b in the fixed part 2 as in the second embodiment prevents the movable part 3 from being exposed out in the diametrical direction and, hence, prevents dust, dirt, etc. from making an ingress into the movable part 3 from outside so that unerring actuation of the drive unit 1 is achievable.

Figure 7A:
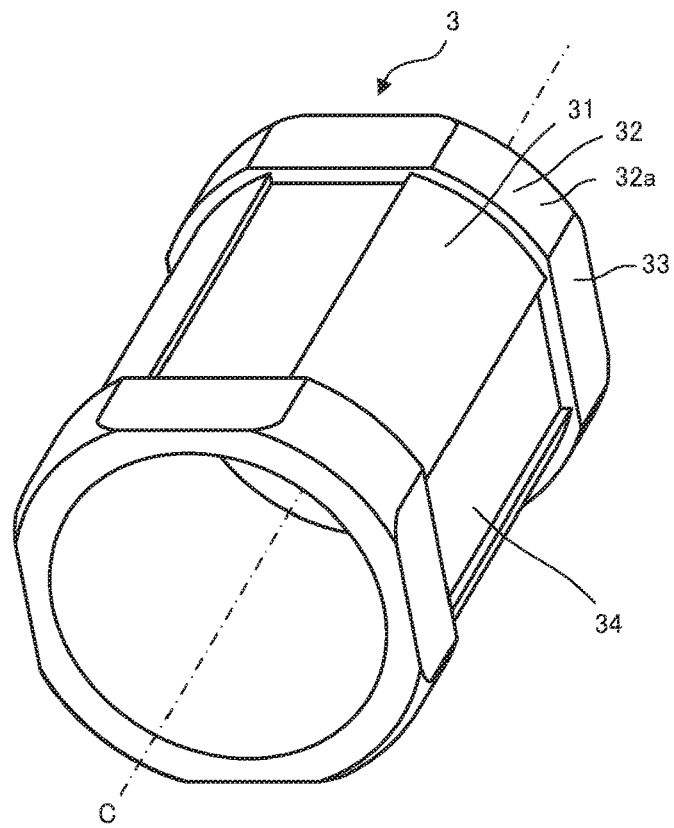
FIGS. 7A and 7B are illustrative of the movable part of the drive unit according to the third embodiment of the invention.
Figure 7B:
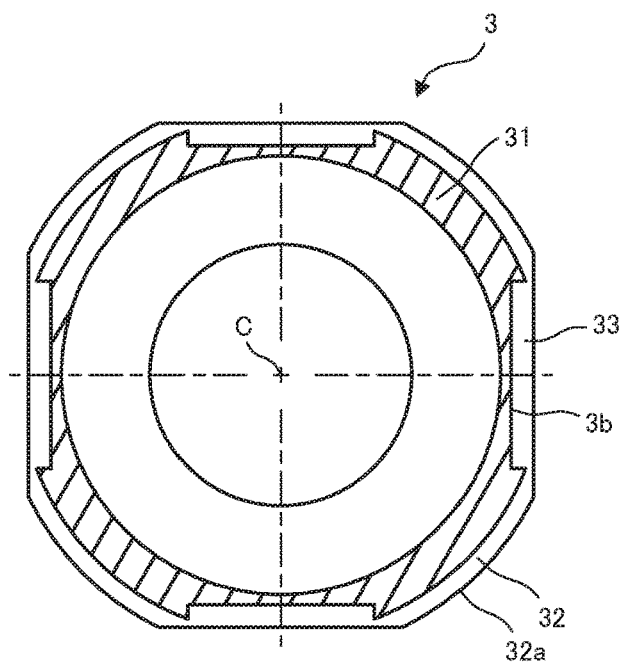

FIGS. 7A and 7B are illustrative of the movable part 3 of the drive unit according to the third embodiment of the invention: FIG. 7A is a perspective view of the movable part 3 of the drive unit according to the third embodiment, and FIG. 7B is a sectional view of the movable part 3 in a direction orthogonal to the axis C.

The drive unit 1 according to the third embodiment has a structure where all the openings 3a formed in the movable part 3 according to the first embodiment are replaced by step portions 34.

In the drive unit 1 according to the third embodiment, as shown in FIGS. 7A and 7B, the movable part 3 is a member having a tubular form. The movable part 3 according to the third embodiment includes a tubular portion 31, protruding edges 32 formed at both ends of the tubular portion 31 in the axial direction of the tubular portion 31 and having an outer diameter larger than the diameter of the tubular portion 31, and a planar portion 33 formed on a part of the outer circumference side of the protruding edge 32. The tubular portion 31 includes a step portion 34. In the third embodiment, there are four step portions 34 provided for each 90° with the axis C of the tubular portion 31 as center. The respective step portions 34 form four diametrically orthogonal planes for each 90° with respect to the center of the axis.

A magnet 12 (not shown) is placed on the step portion 34 as described in the first and second embodiment. In a state where the magnet 12 is placed in the movable part 3, a part of the magnet 12 is positioned in the lightened site such as the opening 2a or recess 2b in the fixed part 2, as shown in FIGS. 1 and 6. In other words, the first distance L1 from the axis C to the diametrically outer surface 121 of the magnet 12 is longer than the second distance L2 from the axis C to the inner circumference surface 23 of the fixed part 2. As the first distance L1 gets longer than the second distance L2, the diameter of the fixed part 2 can be smaller and, hence, the size and weight of the drive unit 1 can be smaller. This ensures that the driving efficiency of the drive unit 1 is boosted up enough to provide rapid movement of the movable part 3.

The formation of the step portion 34 in place of the opening 3a referred to in FIG. 4 dispenses with the step of forming the opening 3a, resulting in ease of formation within a shorter period of time. The formation of the step portion 34 integral with the tubular portion 31 with the axis C as center also contributes to improvements in the strength of the movable part 3.

Figure 8A:
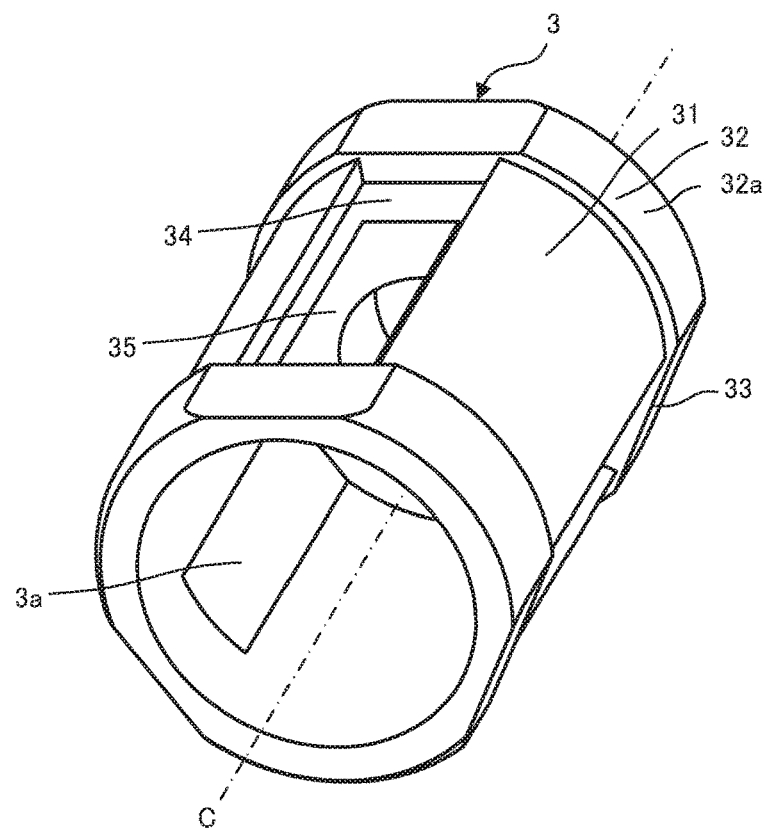
FIGS. 8A and 8B are illustrative of the movable part of the drive unit according to the fourth embodiment of the invention.
Figure 8B:
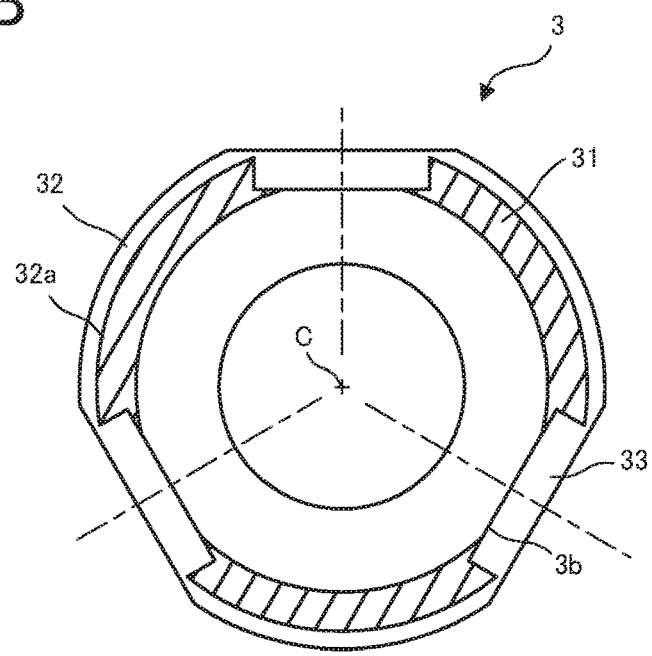

FIGS. 8A and 8B are illustrative of the movable part 3 of the drive unit according to the fourth embodiment of the invention: FIG. 8A is a perspective view of the movable part 3 of the drive unit according to the fourth embodiment, and FIG. 8B is a sectional view of the movable part 3 in a direction orthogonal to the axis C.

The drive unit 1 according to the fourth embodiment has a structure where the number of the step portions 34 for receiving the magnets 12 in the movable part 3 according to the first embodiment is changed. The drive unit 1 according to the fourth embodiment is otherwise the same as that according to the first embodiment.

In the drive unit 1 according to the fourth embodiment shown in FIGS. 8A and 8B, the movable part 3 is a member having a tubular form. The movable part 3 according to the fourth embodiment includes a tubular portion 31, protruding edges 32 formed at both ends of the tubular portion 31 in the axial direction of the tubular portion 31 and having an outer diameter larger than the diameter of the tubular portion 31, a planar portion 33 formed on a part of the outer circumference side of the protruding edge 32, a step portion 34 formed between the planar portions 33 at both the ends in the axial direction of the tubular portion 31, and a small inner-diameter portion 35 formed on one side of the axial direction. A part of the step portion 34 is provided with an opening 3a. In the fourth embodiment, there are three step portions 34 provided for each 120° with the axis C of the tubular portion 31 as center, and a part of each step portion 34 is provided with an opening 3a. The respective step portions 34 form three diametrically orthogonal planes for each 120° with respect to the center of the axis.

A magnet 12 (not shown) is placed on the step portion 34 as in the first and second embodiment. In a state where the magnet 12 is placed in the movable part 3, a part of the magnet 12 is positioned in the lightened site such as the opening 2a or recess 2b in the fixed part 2, as shown in FIGS. 1 and 6. In other words, the first distance L1 from the axis C to the diametrically outer surface 121 of the magnet 12 is longer than the second distance L2 from the axis C to the inner circumference surface 23 of the fixed part 2. As the first distance L1 gets longer than the second distance L2, the diameter of the fixed part 2 can be smaller and, hence, the size and weight of the drive unit 1 can be smaller. This ensures that the driving efficiency of the drive unit 1 is boosted up enough to provide rapid movement of the movable part 3.

Forming three step portions 34 in place of the four step portions 34 shown in FIG. 1 makes it possible to shorten the time taken by the steps of forming the step portions 34 and mounting the magnet 12 in place, resulting in ease of formation within a shorter period of time. A decrease in the number of magnets 12 used leads to cost reductions.

Figure 9:
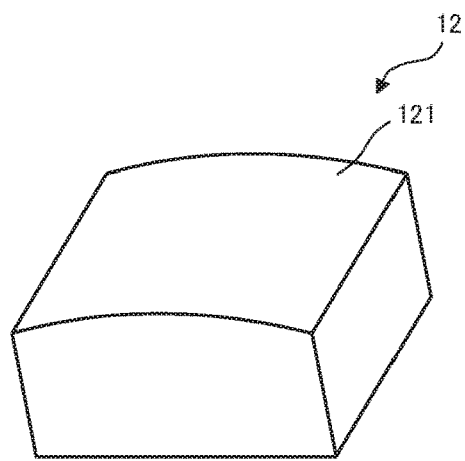
FIG. 9 is illustrative of the magnet used in the drive unit according to the fifth embodiment of the invention.
Figure 10:
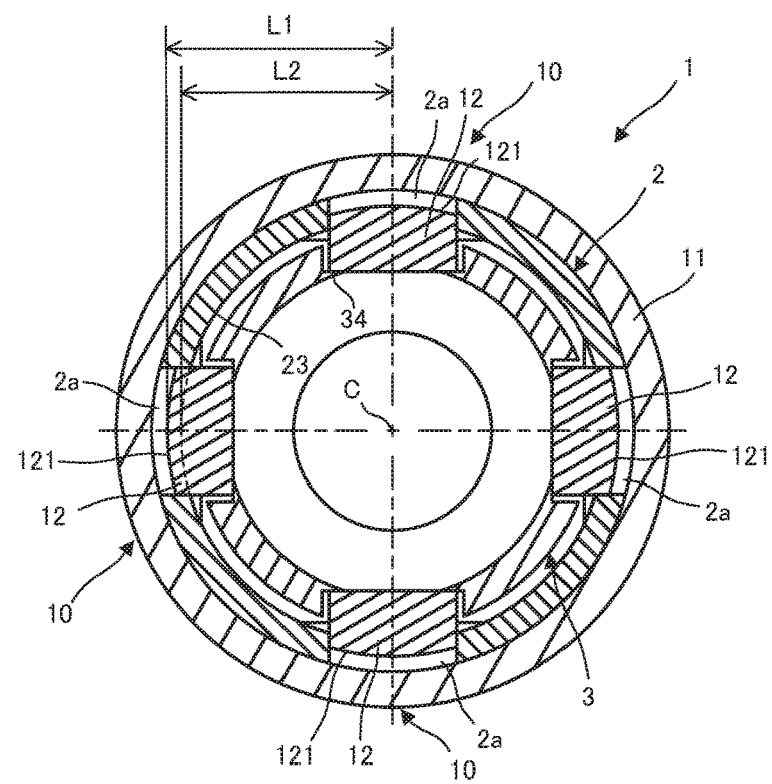
FIG. 10 is a sectional view of the drive unit according to the fifth embodiment as being orthogonal to an axis.

FIG. 9 is illustrative of the magnet 12 used with the drive unit according to the fifth embodiment of the invention, and FIG. 10 is a sectional view of the drive unit 1 according to the fifth unit, as taken on a section orthogonal to the axis.

In the drive unit 1 according to the fifth embodiment, the diametrically outer surface 121 of the magnet 12 is configured into a cylindrical shape, as shown in FIG. 9. Note here that the diametrically inner surface is a plane.

In the firth embodiment, the magnet 12 is placed in each step portion 34 as shown in FIG. 10. In s state where the magnet 12 is placed in the movable part 3, a part of the magnet 12 is positioned in the lightened site such as the opening 2a in the fixed part 2. In other words, the first distance L1 from the axis C to the diametrically outer surface 121 of the magnet 12 is longer than the second distance L2 from the axis C to the inner circumference surface 23 of the fixed part 2. As the first distance L1 gets longer than the second distance L2, the diameter of the fixed part 2 can be smaller and, hence, the size and weight of the drive unit 1 can be smaller. This ensures that the driving efficiency of the drive unit 1 is boosted up enough to provide rapid movement of the movable part 3.

The cylindrical configuration of the diametrically outer surface 121 of the magnet 12 conforms well to the inner circumference surface 23 of the cylindrical coil 11, resulting in an increased driving force. In addition, this ensures that the diametrically outer surface 121 of the magnet 12 and the inner circumference surface 23 of the coil 11 in opposition thereto are configured into a similar shape having a similar surface curvature, again resulting in an increased driving force.

Figure 11:
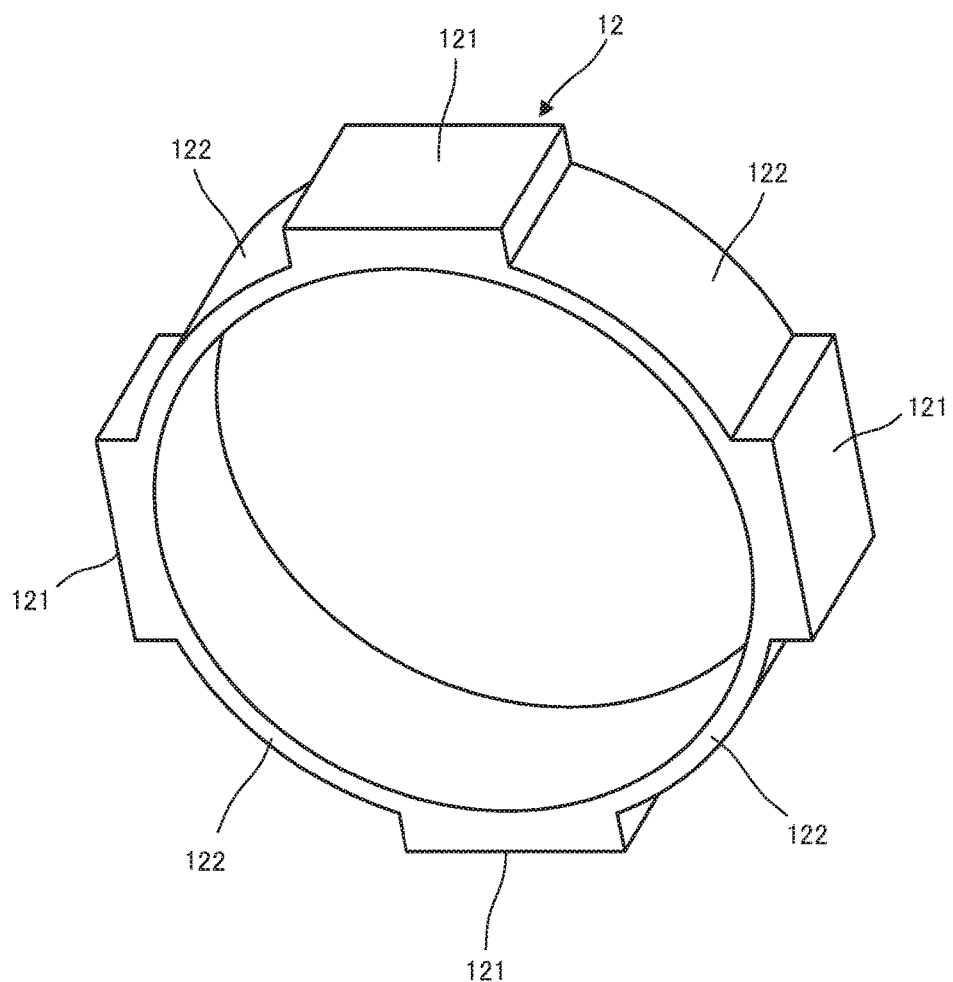
FIG. 11 is illustrative of the magnet used in the drive unit according to the sixth embodiment of the invention.
Figure 12A:
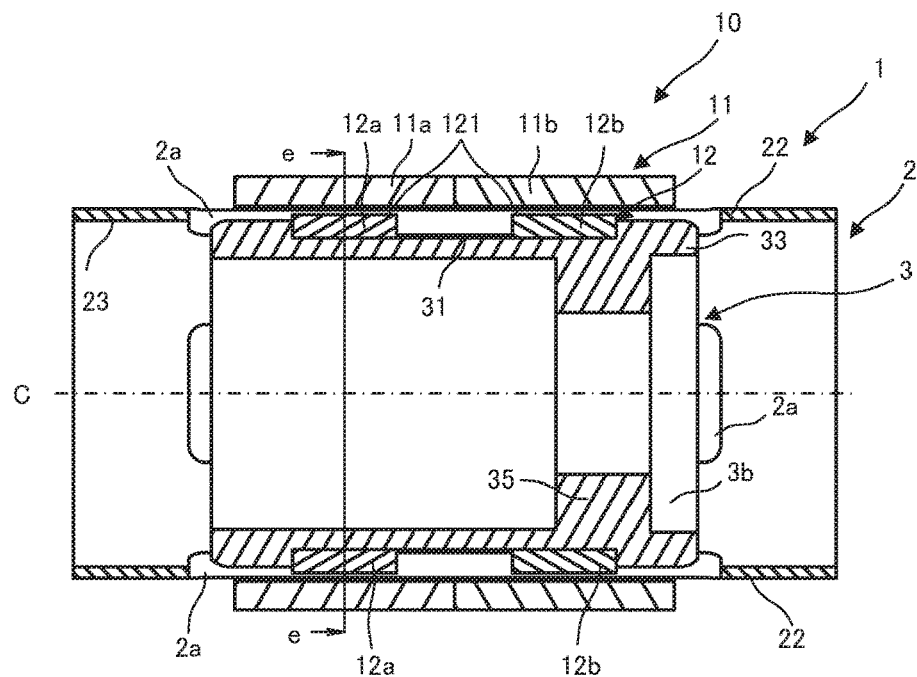
FIGS. 12A and 12B are illustrative of the drive unit according to the sixth embodiment.
Figure 12B:
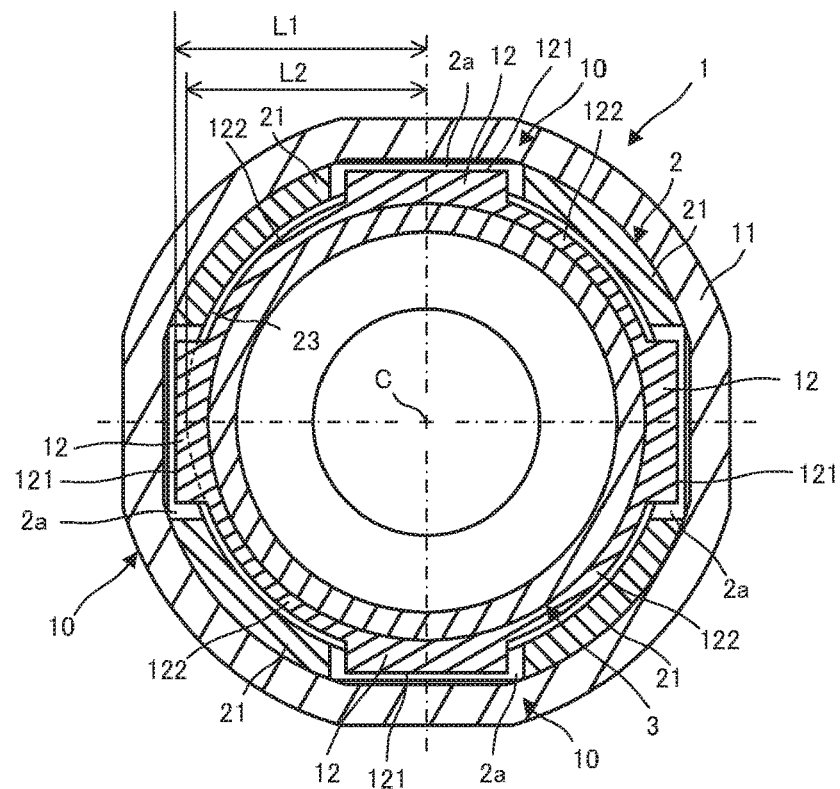

FIG. 11 is illustrative of the magnet 12 used with the drive unit according to the sixth embodiment of the invention. FIGS. 12A and 12B are illustrative of the drive unit 1 according to the sixth embodiment: FIG. 12A is a sectional view of the drive unit 1 according to the sixth embodiment including its axis, and FIG. 12B is a sectional view of FIG. 12A as taken on section e-e.

In the drive unit 1 according to the sixth embodiment, the magnet 12 is configured into an annular shape including connectors 122, as shown in FIG. 11. In the sixth embodiment, the diametrically magnetized magnets 12 are located for each 90° with respect to the axis, and the adjacent magnets are connected together by the associated connectors 122. Note here that the inner circumference side may be in a cylindrical configuration. The magnet 12 may have been integral with the connectors 122 or, alternatively, the magnet and connectors formed of separate materials may be joined together in situ.

As shown in FIGS. 12A and 8B, the magnet 12 is placed on the outer circumference of the tubular portion 31 of the movable part 3. The diametrically outer surface 121 of the magnet may be similar in shape to the inner circumference surface 23 of the coil 11 in opposition thereto; in the sixth embodiment, that surface 121 has a planar form as is the case with the first embodiment shown in FIG. 1. In a state where the magnet 12 is placed in the movable part 3, a part of the magnet 12 is positioned in the opening 2a in the fixed part 2. In other words, the first distance L1 from the axis C to the diametrically outer surface 121 of the magnet 12 is longer than the second distance L2 from the axis C to the inner circumference surface 23 of the fixed part 2. As the first distance L1 gets longer than the second distance L2, the diameter of the fixed part 2 can be smaller and, hence, the size and weight of the drive unit 1 can be smaller. This ensures that the driving efficiency of the drive unit 1 is boosted up enough to provide rapid movement of the movable part 3.

Figure 13:
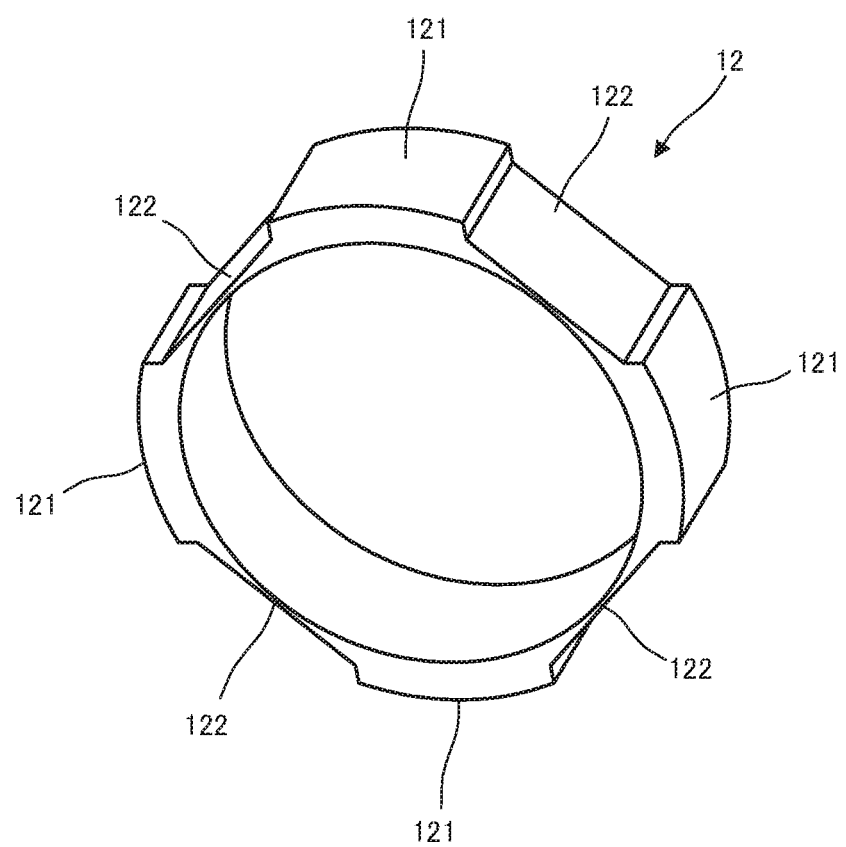
FIG. 13 is illustrative of the magnet used in the drive unit according to the seventh embodiment of the invention.
Figure 14A:
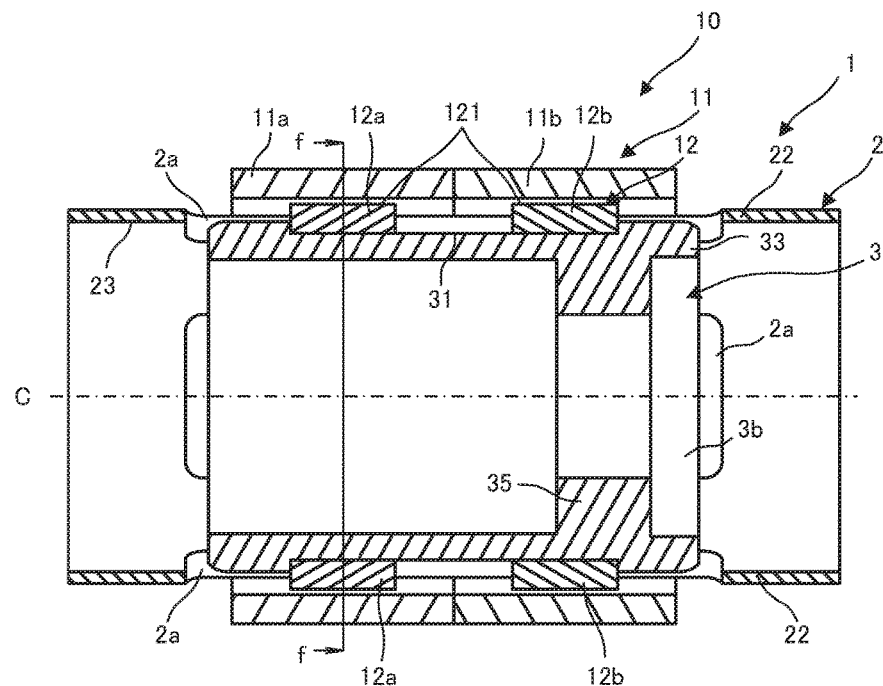
FIGS. 14A and 14B are illustrative of the drive unit according to the seventh embodiment.
Figure 14B:
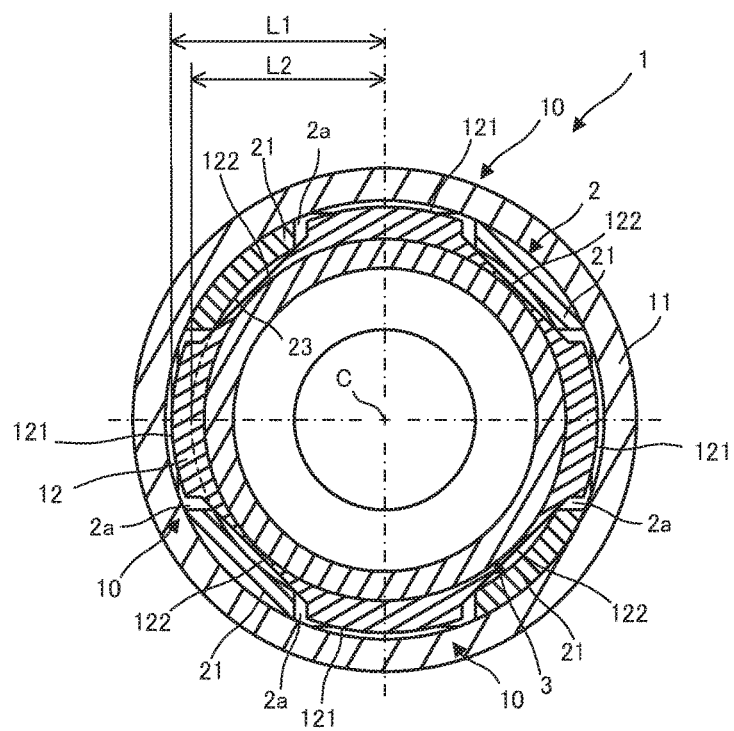

FIG. 13 is illustrative of the magnet 12 used with the drive unit according to the seventh embodiment of the invention. FIGS. 14A and 14B are illustrative of the drive unit 1 according to the seventh embodiment: FIG. 14A is a sectional view of the drive unit 1 according to the seventh embodiment including its axis, and FIG. 14B is a sectional view of FIG. 14A as taken on section f-f.

In the drive unit 1 according to the seventh embodiment, the magnet 12 includes connectors 122, and is configured into an annular shape, as shown in FIG. 13. In the seventh embodiment, the diametrically magnetized magnets 12 are located for each 90° with respect to the axis, and the adjacent magnets are connected together by the associated connectors 122. The magnet 12 may have been integral with the connectors 122 or, alternatively, the magnet and connectors formed of separate materials may later be joined together in situ. In the seventh embodiment, the connectors 122 for the magnet 12 are formed of planes on the outer circumference side so that they are thinner in the intermediate positions, contributing much to weight reductions. Note here that the inner circumference side may be in a cylindrical shape.

As shown in FIGS. 14A and 14B, the magnet 12 is placed on the outer circumference of the tubular portion 31 of the movable part 3. The diametrically outer surface 121 of the magnet may be similar in shape to the inner circumference surface 23 of the coil 11 in opposition thereto; in the seventh embodiment, that surface 121 has a cylindrical form as is the case with the fifth embodiment shown in FIG. 10. In a state where the magnet 12 is placed in the movable part 3, a part of the magnet 12 is positioned in the opening 2a in the fixed part 2. In other words, the first distance L1 from the axis C to the diametrically outer surface 121 of the magnet 12 is longer than the second distance L2 from the axis C to the inner circumference surface 23 of the fixed part 2. As the first distance L1 gets longer than the second distance L2, the diameter of the fixed part 2 can be smaller and, hence, the size and weight of the drive unit 1 can be smaller. This ensures that the driving efficiency of the drive unit 1 is boosted up enough to provide rapid movement of the movable part 3.

Figure 15:
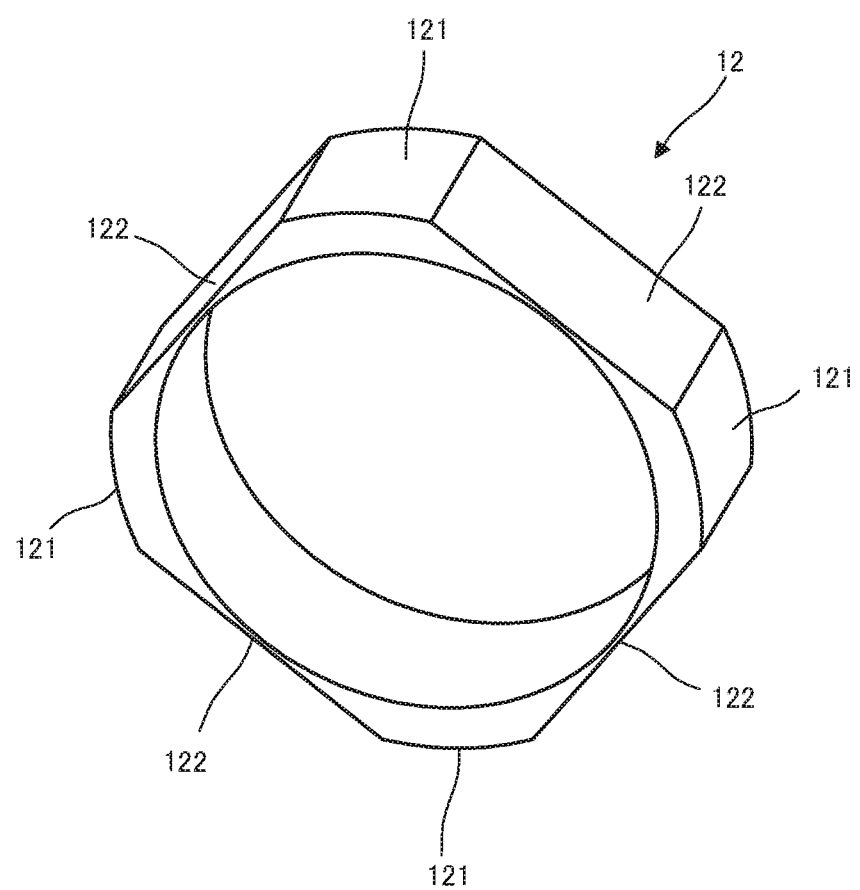
FIG. 15 is illustrative of the magnet used in the drive unit according to the eighth embodiment of the invention.
Figure 16A:
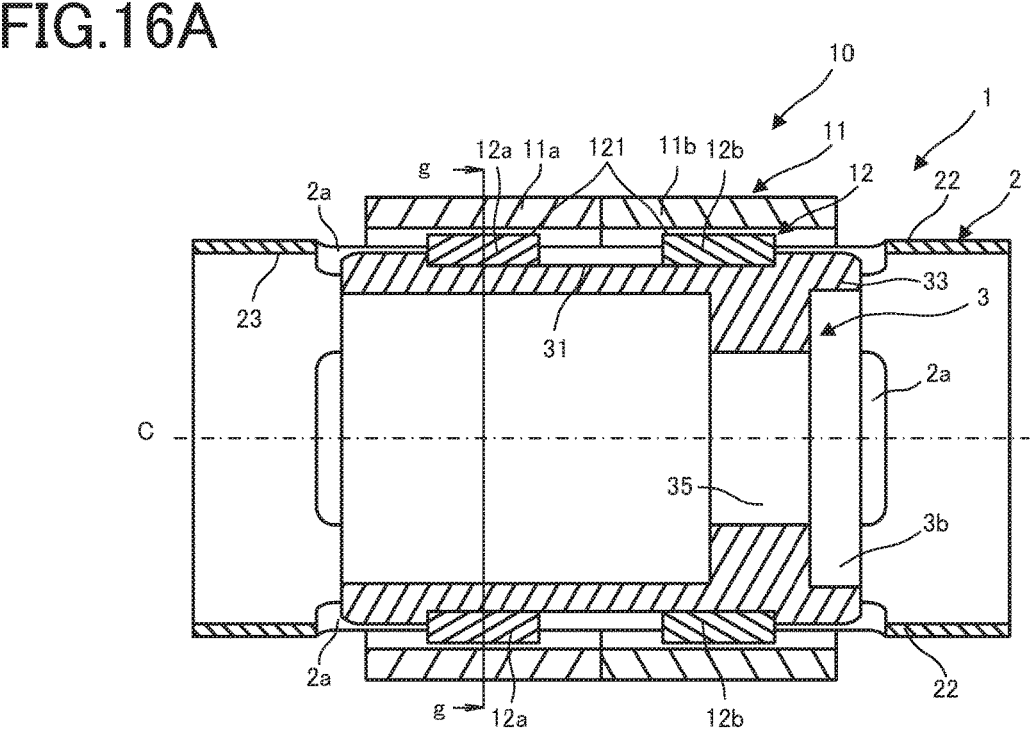
FIGS. 16A and 16B are illustrative of the drive unit according to the eighth embodiment.
Figure 16B:
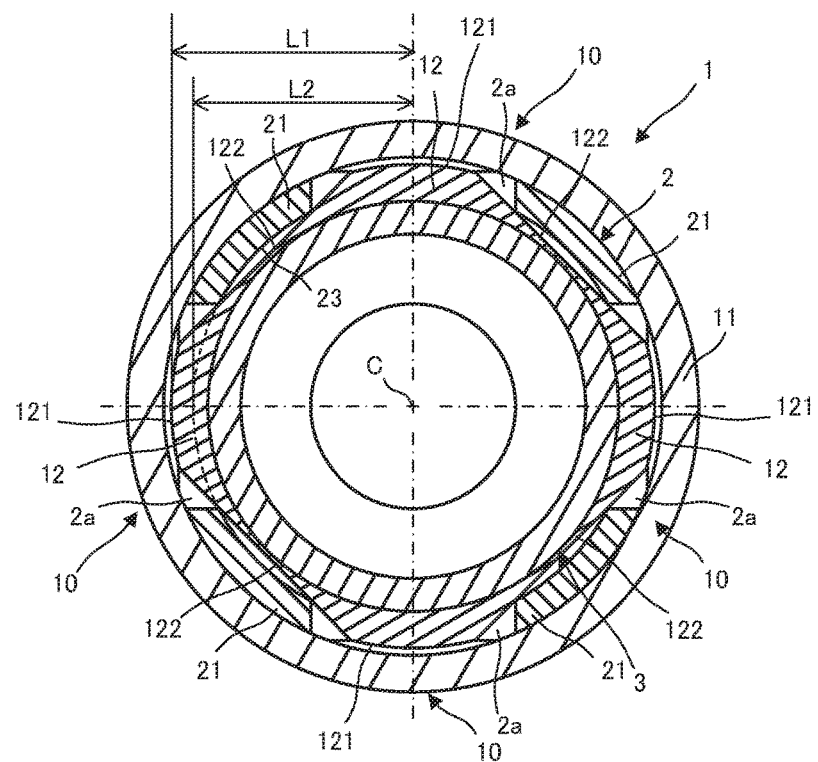

FIG. 15 is illustrative of the magnet 12 used with the drive unit according to the eighth embodiment of the invention. FIGS. 16A and 16B are illustrative of the drive unit 1 according to the eighth embodiment: FIG. 16A is a sectional view of the drive unit 1 according to the eighth embodiment including its axis, and FIG. 16B is a sectional view of FIG. 16A as taken on section g-g.

In the drive unit 1 according to the eighth embodiment, the magnet 12 includes connectors 122, and is configured into an annular shape, as shown in FIG. 15. In the eighth embodiment, the diametrically magnetized magnets 12 are located for each 90° with respect to the axis, and the adjacent magnets are connected together by the associated connectors 122. The magnet 12 may have been integral with the connectors 122 or, alternatively, the magnet and connectors formed of separate materials may later be joined together in situ. In the eighth embodiment, the connector 122 for the magnet 12 on the outer circumference side is formed of a plane running to the diametrically outer surface 121 of the magnet 12 so that it gets thinner in the intermediate position, leading just only to weight reductions but also to ease of outer circumference processing. Note here that the inner circumference side may be in a cylindrical shape.

As shown in FIGS. 16A and 16B, the magnet 12 is placed on the outer circumference of the tubular portion 31 of the movable part 3. The diametrically outer surface 121 of the magnet may be similar in shape to the inner circumference surface 23 of the coil 11 in opposition thereto; in the eighth embodiment, that surface 121 has a cylindrical form as is the case with the fifth embodiment shown in FIG. 10. In a state where the magnet 12 is placed in the movable part 3, a part of the magnet 12 is positioned in the opening 2a in the fixed part 2. In other words, the first distance L1 from the axis C to the diametrically outer surface 121 of the magnet 12 is longer than the second distance L2 from the axis C to the inner circumference surface 23 of the fixed part 2. As the first distance L1 gets longer than the second distance L2, the diameter of the fixed part 2 can be smaller and, hence, the size and weight of the drive unit 1 can be smaller. This ensures that the driving efficiency of the drive unit 1 is boosted up enough to provide rapid movement of the movable part 3.

Figure 17:
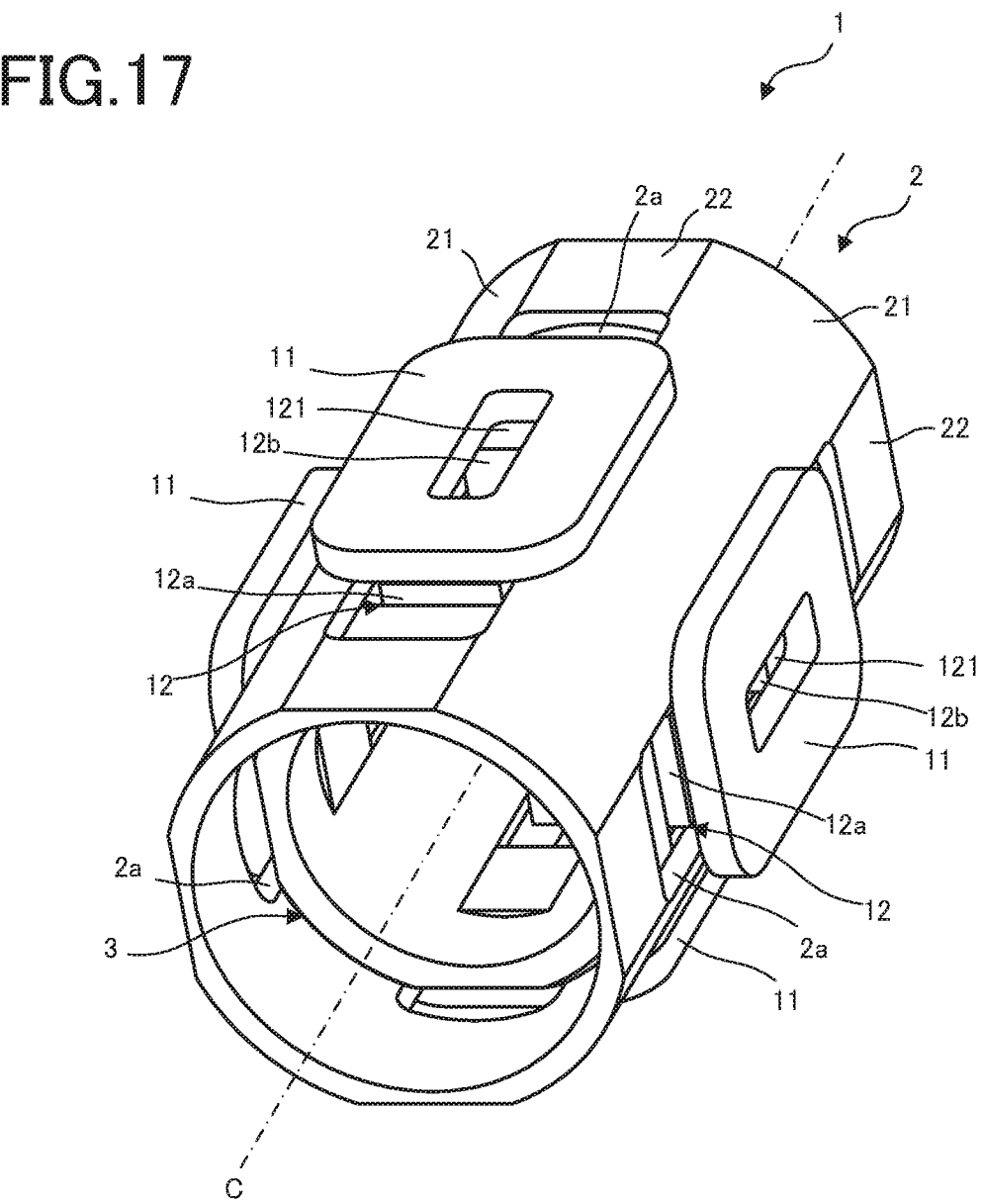
FIG. 17 is a perspective view of the magnet used in the drive unit according to the ninth embodiment of the invention.
Figure 18A:
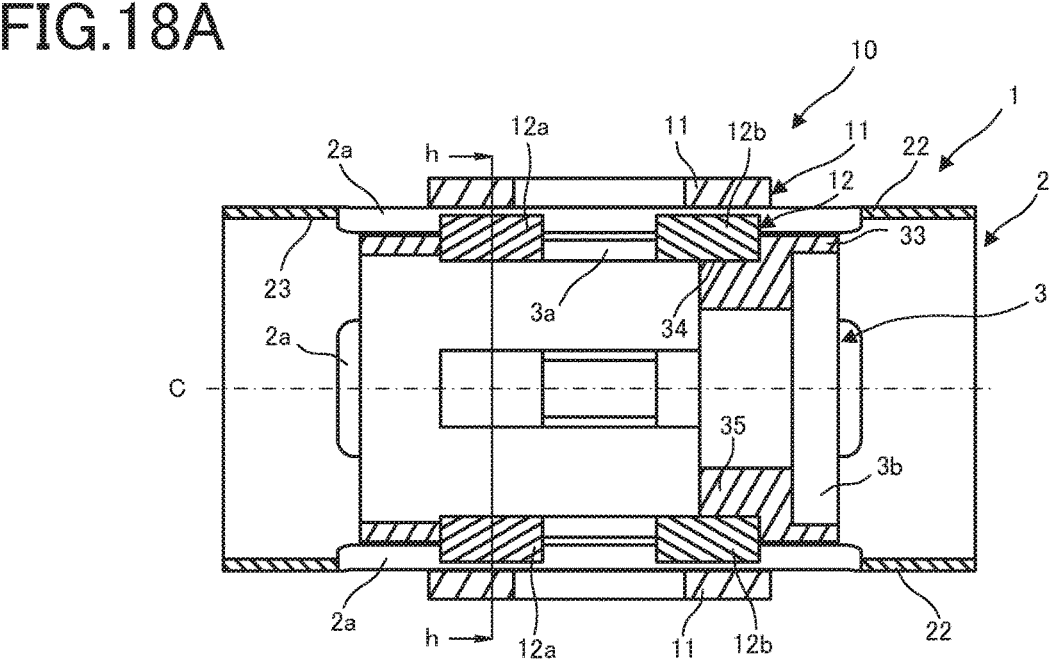
FIGS. 18A and 18B are sectional views of the drive unit according to the ninth embodiment.
Figure 18B:
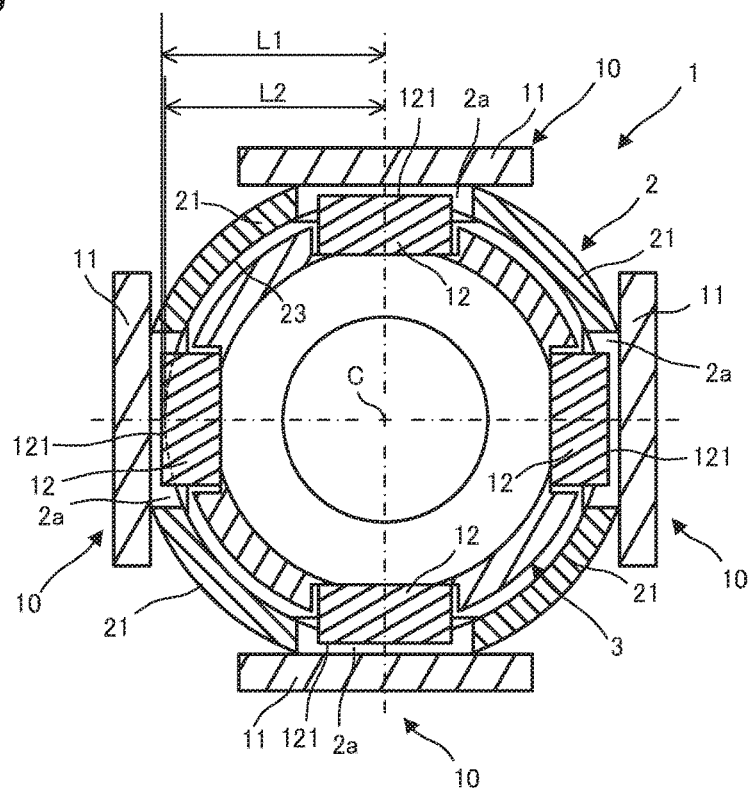

FIG. 17 is a perspective view of the drive unit 1 according to the ninth embodiment of the invention. FIGS. 18A and 18B are sectional views of the drive unit 1 according to the ninth embodiment: FIG. 18A is a sectional view of the drive unit 1 according to the ninth embodiment including its axis, and FIG. 18B is a sectional view of FIG. 18A as taken on section h-h.

In the drive unit 1 according to the ninth embodiment, there are four coils 11 located for each 90° with respect to the axis: one per a set of axially located magnets 12. In other words, there are four coils 11 and eight magnets 12 provided. The diametrically outer surface 121 of the magnet 12 and the coil 11 in opposition to the diametrically outer surface 121 of the magnet 12 are each formed of a plane.

With the drive unit 1 having such structure, the placement of the coils 11 having a simple shape is all that is needed for assembling, making sure increased productivity, ease of assembling, and a curtailment of assembling time.

Figure 19:
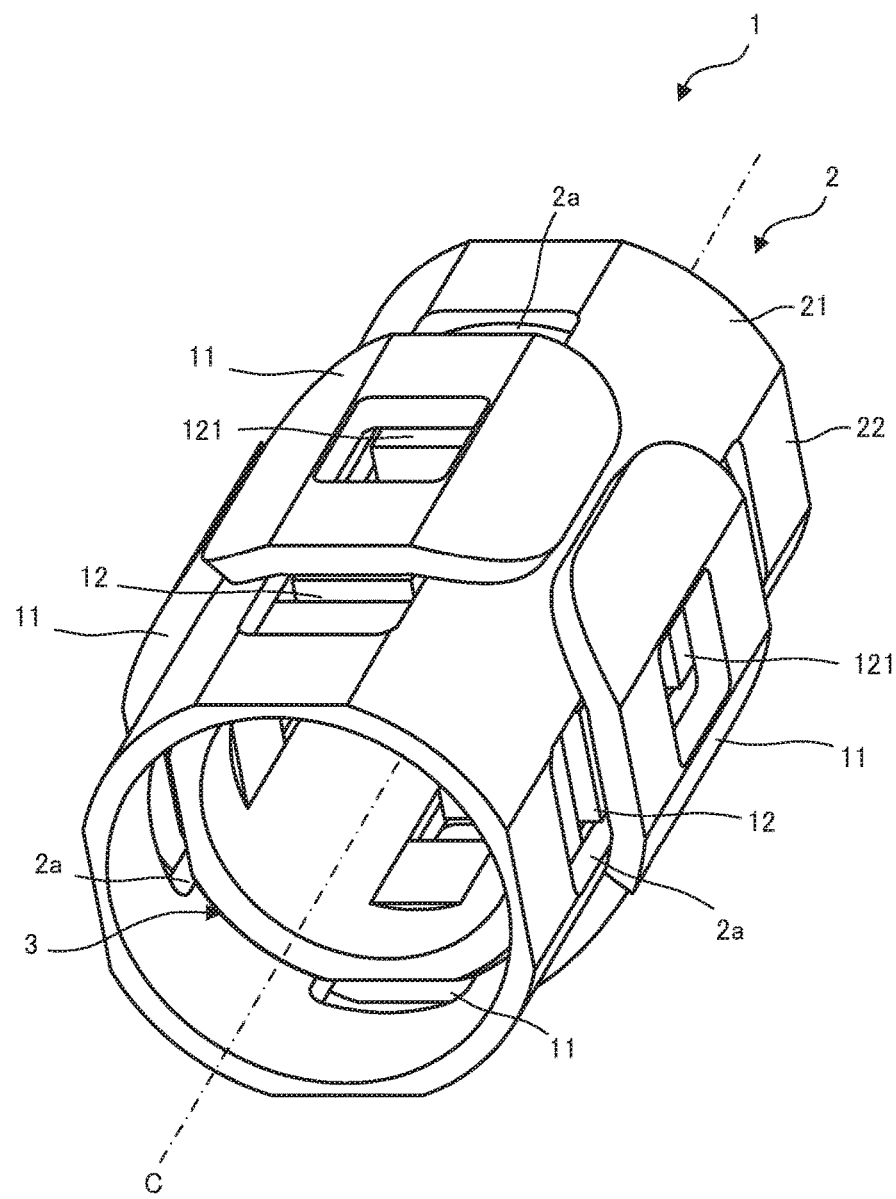
FIG. 19 is a perspective view of the drive unit according to the $10^{th}$ embodiment of the invention.
Figure 20A:
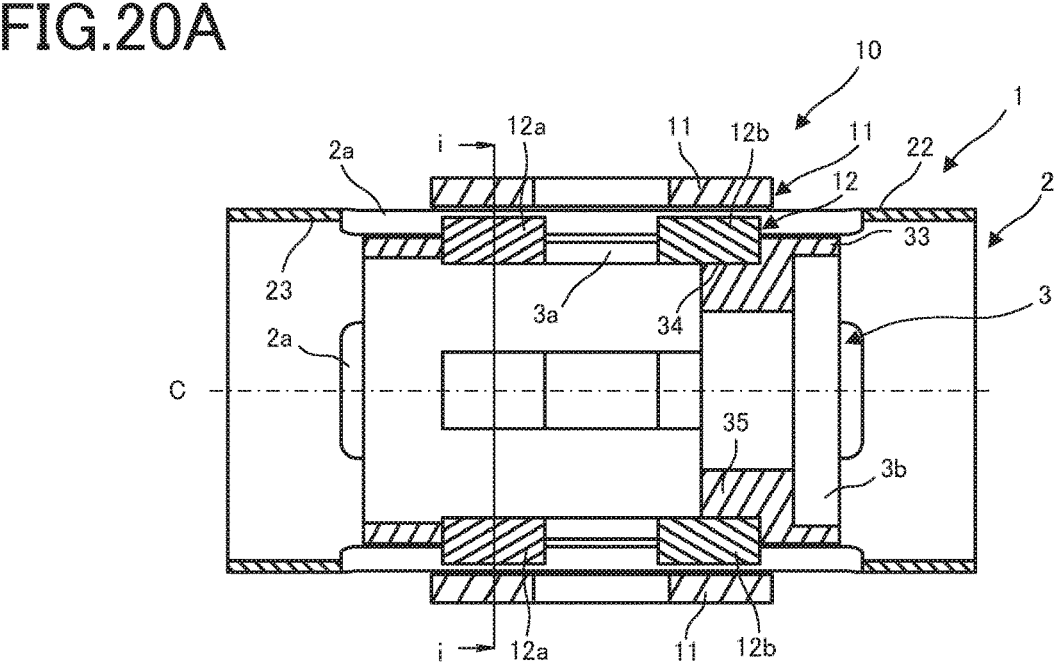
FIGS. 20A and 20B are sectional views of the drive unit according to the $10^{th}$ embodiment.
Figure 20B:
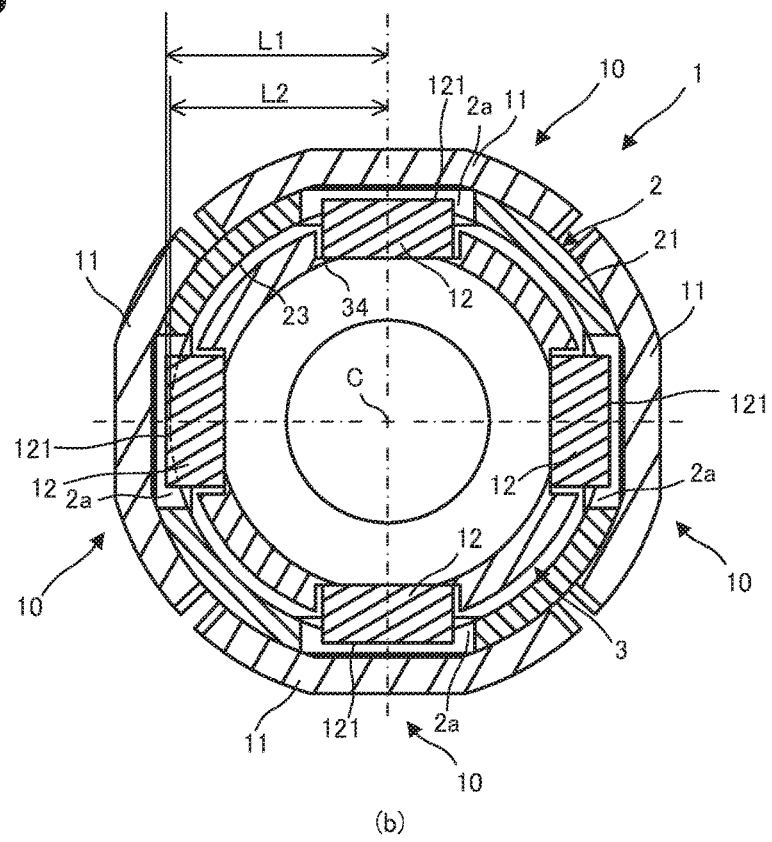

FIG. 19 is a perspective view of the drive unit 1 according to the 10$^{th}$ embodiment of the invention. FIGS. 20A and 20B is a sectional view of the drive unit 1 according to the 10$^{th}$ embodiment: FIG. 20A is a sectional view of the drive unit 1 according to the 10$^{th}$ embodiment including its axis, and FIG. 20B is a sectional view of FIG. 20A as taken on section i-i.

In the drive unit 1 according to the 10$^{th}$ embodiment, there are four coils 11 located for each 90° with respect to the axis: one per a set of axially located magnets 12. In other words, there are four coils 11 and eight magnets 12 provided. The diametrically outer surface 121 of the magnet 12 and the coil 11 in opposition to the diametrically outer surface 121 of the magnet 12 are each formed of a plane. The coil 11 extends from the planar portion 22 of the fixed part 2 onto the tubular portion 21 adjacent to it on both sides, and a portion of the coil 11 located along the outer circumference side of the tubular portion 21 is configured in a cylindrical shape.

The drive unit 1 according to the 10$^{th}$ embodiment makes sure increased productivity, ease of assembling, and a curtailment of assembling time. With the drive unit 1 according to the 10$^{th}$ embodiment, it is also possible to boost up driving force because the coil 11 gets larger than that according to the ninth embodiment.

Figure 21:
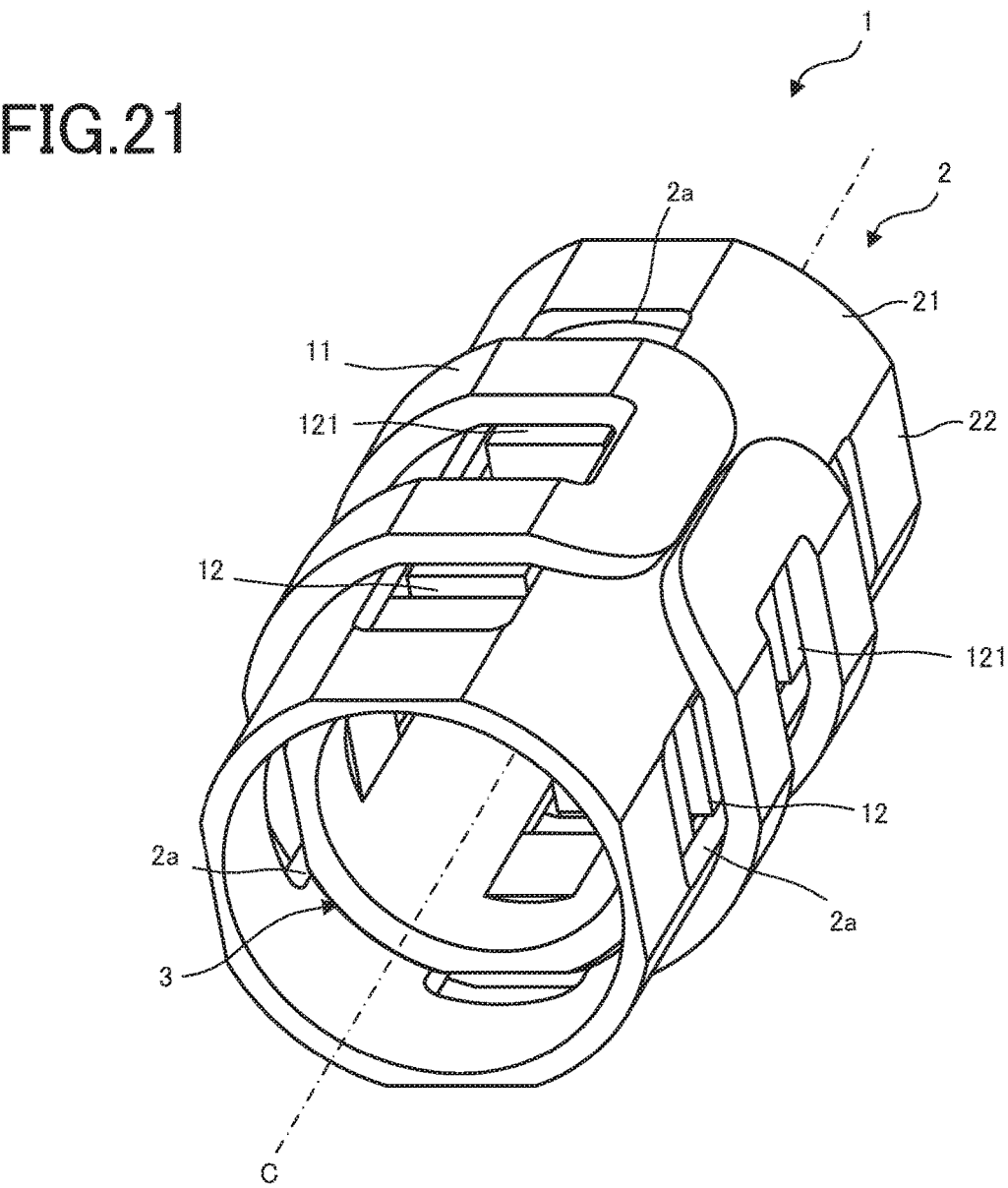
FIG. 21 is a perspective view of the drive unit according to the $11^{th}$ embodiment of the invention.
Figure 22A:
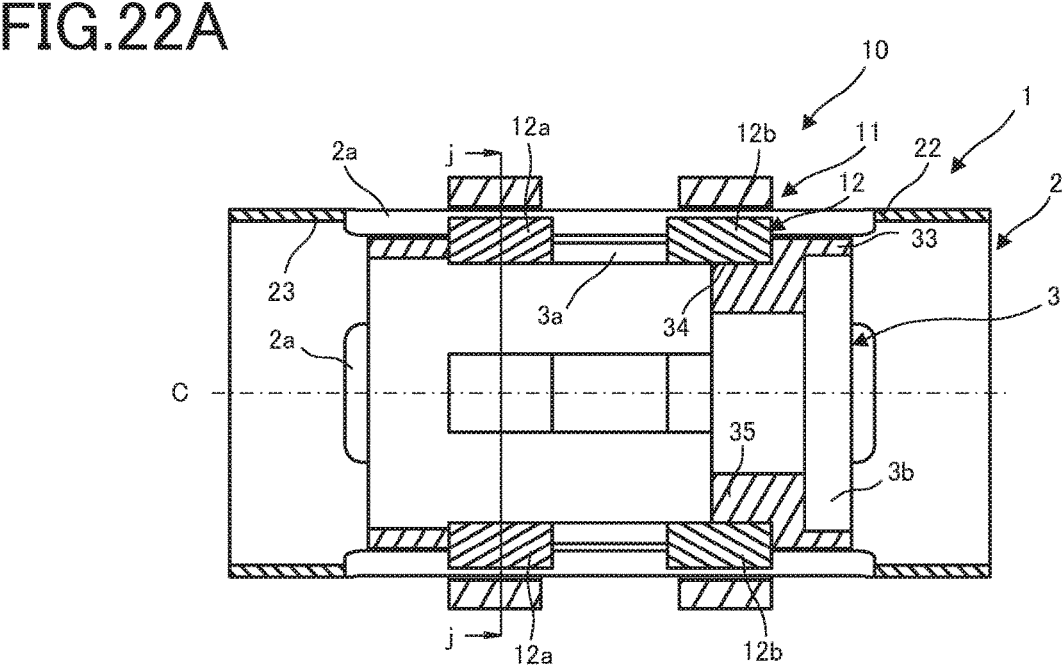
FIGS. 22A and 22B are sectional views of the drive unit according to the $11^{th}$ embodiment.
Figure 22B:
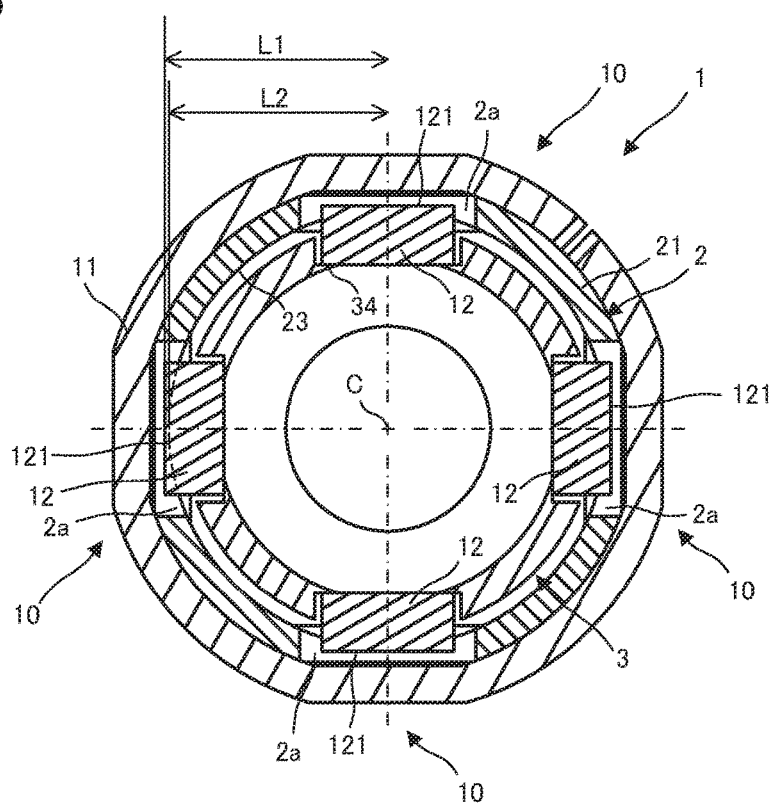

FIG. 21 is a perspective view of the drive unit 1 according to the 11$^{th}$ embodiment of the invention. FIGS. 22A and 22B is a sectional view of the drive unit 1 according to the 11$^{th}$ embodiment: FIG. 22A is a sectional view of the drive unit 1 according to the 11$^{th}$ embodiment including its axis, and FIG. 22B is a sectional view of FIG. 22A as taken on section j-j.

In the drive unit 1 according to the 11$^{th}$ embodiment, one coil 11 is folded along and located on the outer circumference of the fixed part 2. Specifically, a portion of the coil 11 opposite to the diametrically outer surface 121 of the magnet 12 is formed of a plane, and a portion of the coil 11 located along the tubular portion 21 is configured into a cylindrical shape.

The placement of one coil 11 is all that is needed to assemble the drive unit 11 according to the 11$^{th}$ embodiment, resulting in increased productivity, ease of assembling, and a curtailment of assembling time.

Figure 23:
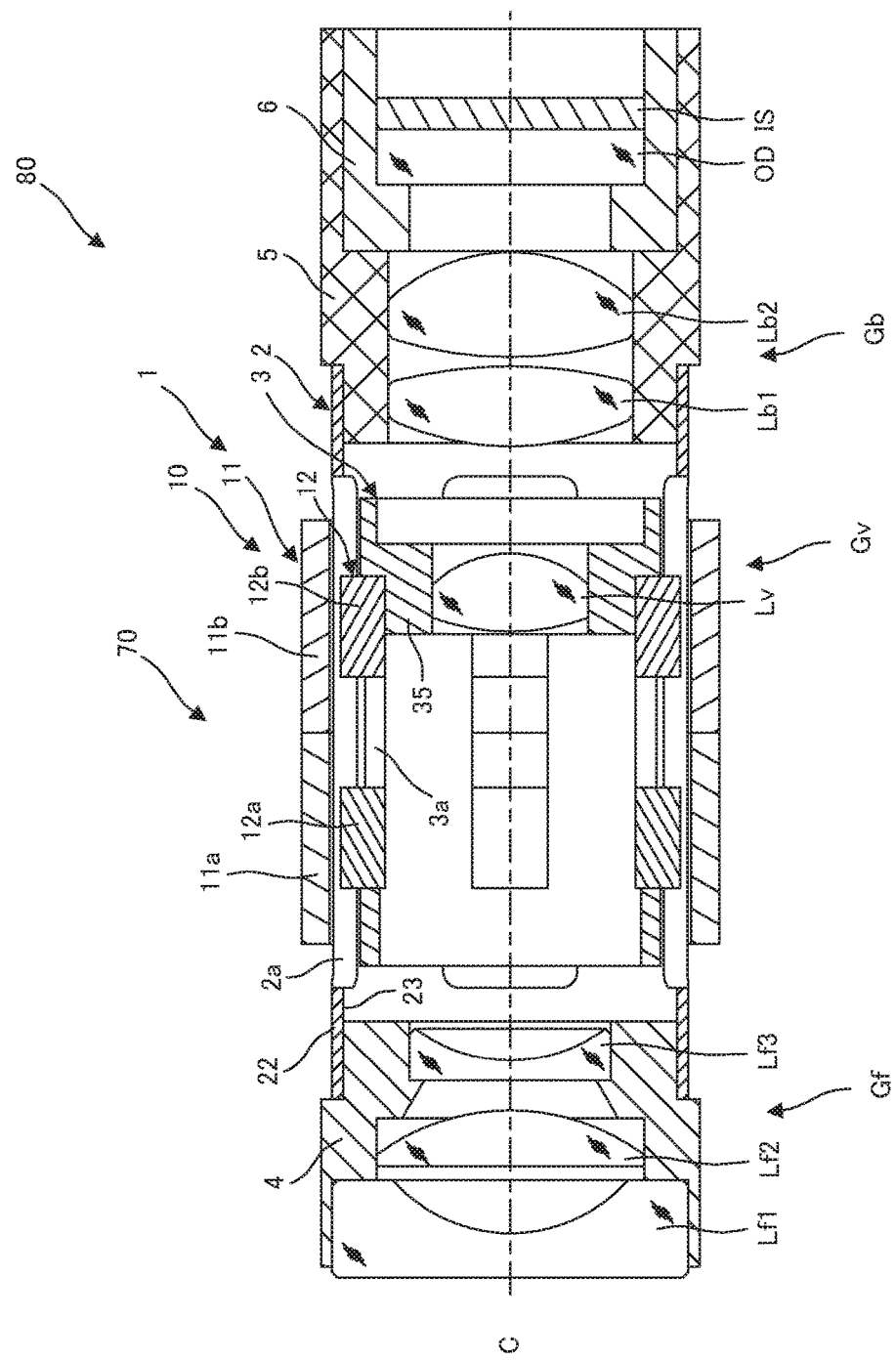
FIG. 23 is a sectional view of the optical unit and imaging apparatus according to one embodiment of the invention.

FIG. 23 is illustrative of the optical unit 70 and imaging apparatus 80 according to one embodiment of the invention.

The optical unit 70 includes a drive unit 1 similar to that according to the first embodiment, and a moving lens group Gv attached to the small inner-diameter portion 35 of the drive unit 1. The center axis O of a moving lens Lv should preferably be the same as the axis C of the drive unit 1.

The optical unit 70 is designed such that with the moving lens Lv attached to the moving lens group Gv, the movable part 3 is movable relative to the fixed part 2 in the axis C direction. Movement of the movable part 3 relative to the fixed part 2 allows for movement of the focal position of the optical unit 70.

The imaging apparatus 80 includes an optical unit 70, a front lens group Gf attached to a fixed part 2 on the object side of the optical unit 70, a back lens group Gb attached to the fixed part 2 on the image side of the optical unit 70, and an imaging device (sensor) IS having a light-receiving site located on an image plane.

The front lens group Gf according to the embodiment described herein includes a first front lens Lf1, a second front lens Lf2 and a third front lens Lf3 held in a front group frame 4 attached as by press fitting or bonding to the fixed part 2. The back lens group Gb according to the embodiment described herein includes a first back lens Lb1 and a second back lens Lb2 held in a back group frame 5 attached as by press fitting or bonding to the fixed part 2. In the embodiment described herein, the imaging device IS is any type of image sensor such as CCD or CMOS, and is held in an imaging device frame 6. On the object side of the imaging device IS, a filter or cover glass or other optical elements OD are positioned in adjoining relations.

It is here to be appreciated that the lens arrangement of the front lens group Lf, back lens group Lb and moving lens group Gv is not limited to the embodiment; it may be modified as required. In the embodiment described herein, the front group frame 4 and back group frame 5 are bonded to the fixed part 2 and the imaging device frame 6 is held in the back group frame 5 as mentioned above; however, one or more of these frames may be collectively taken as a part of the fixed part. In this case, it is contemplated that the first distance from the axis C to the diametrically outer surface of the first magnet 12a, and the second magnet 12b is longer than the second distance from the axis C to the inner circumference surface with respect to the maximum outer diameter that the fixed part has.

Referring to the imaging apparatus 80 according to the embodiment described herein, it is when the movable part 3 is positioned on the most image side of the movable range that the imaging magnification gets highest, and it is when the movable part 3 is positioned on the most object side that the imaging magnification gets lowest. To put it another way, it is when the movable part 3 is positioned on the most image side of the movable range that the focal length gets longest and there is a telephoto end state created with a narrow field of view, and it is when the movable part 3 is positioned on the most object side of the movable range that the focal length gets shortest and there is a wide-angle end state created with a wide field of view.

Thus, reductions in the size and weight of the drive unit 1 permit for reductions in the size and weight of the imaging apparatus 80, and movement of the movable part 3 relative to the fixed part 2 permits for rapid zoom change of the imaging apparatus 80.

In this conjunction, such imaging apparatus 80 as described above may be used with an electronic camera apparatus, especially a digital camera or a video camera, as embodied below.

Figure 24:
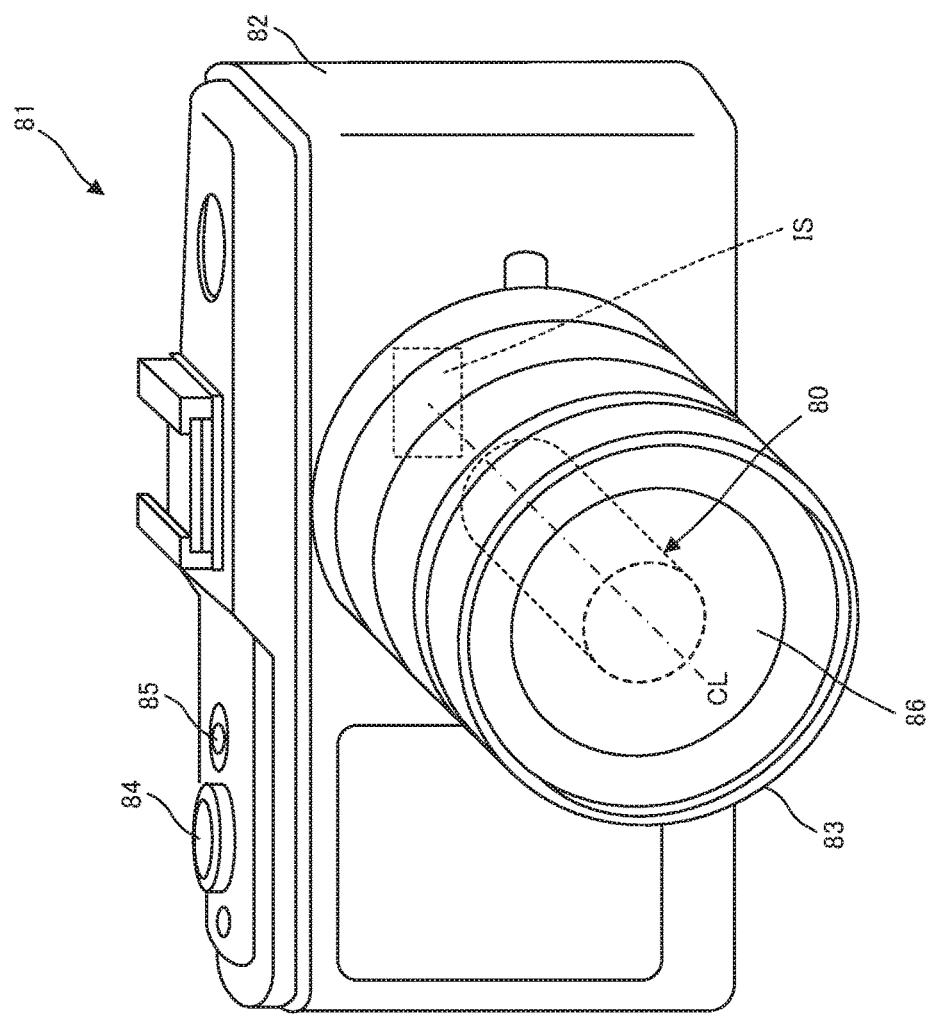
FIG. 24 is illustrative of one example of the digital camera including the imaging apparatus according to one embodiment of the invention.

FIG. 24 is illustrative of one example of the digital camera 81 including the imaging apparatus 80 according to the embodiment described herein.

The imaging apparatus 80 may be used with some products such as a digital camera 81, a digital video camera, and a cellular phone. An example of application of the imaging apparatus 80 according to the embodiment described herein to the digital camera 81 is now explained.

As shown in FIG. 24, the digital camera 81 according to the embodiment described herein includes a camera body 82, and a lens barrel 83 in the form of an interchangeable lens. Note here that the camera body 82 may be detachable from, or integral with, the lens barrel 83.

In the camera body 82, there is an imaging device IS located for electronic taking and recording of subject images. On the light-receiving site of the imaging device IS, there are multiple elements arrayed in a planar form to produce out electric singles in response to incident light at a given timing. The lens barrel 83 is provided with a plurality of objective lenses 86 along the direction of an optical axis CL, and includes the optical unit 70 shown in FIG. 23. That is, a part of the camera body 82 and lens barrel 83 makes up the imaging apparatus 80. Note here that the front lens group Gf shown in FIG. 23 may be located in the lens barrel 83, and the optical unit 70 and back lens group Gb shown in FIG. 23 may be located in the camera body 82.

Mounted on the top of the camera body 82 are a release switch 84 through which a camera operator enters an imaging instruction in it, and a power source switch 85 through which the camera operator turns on or off the camera body 82.

In the embodiment described herein, the release switch 84 is a push-button switch. Upon a semi-depression of the release switch 84, the imaging apparatus 80 is actuated for autofocus or like other operation and upon transition from the semi-depression to a full-depression of the release switch 84, the imaging apparatus 80 is actuated to record images. Note here that a touch-sensor switch or the like may be used in place of the push-button release switch 84.

Mounted on the back of the camera (not shown) are an image display unit, a zooming operation instruction means for giving a zooming instruction to the imaging apparatus 80, etc. Mounted in the camera body 82 are a battery space for storing a primary or secondary battery for power supply and a recording medium space for storing a flash memory adapted to record images.

Figure 25:
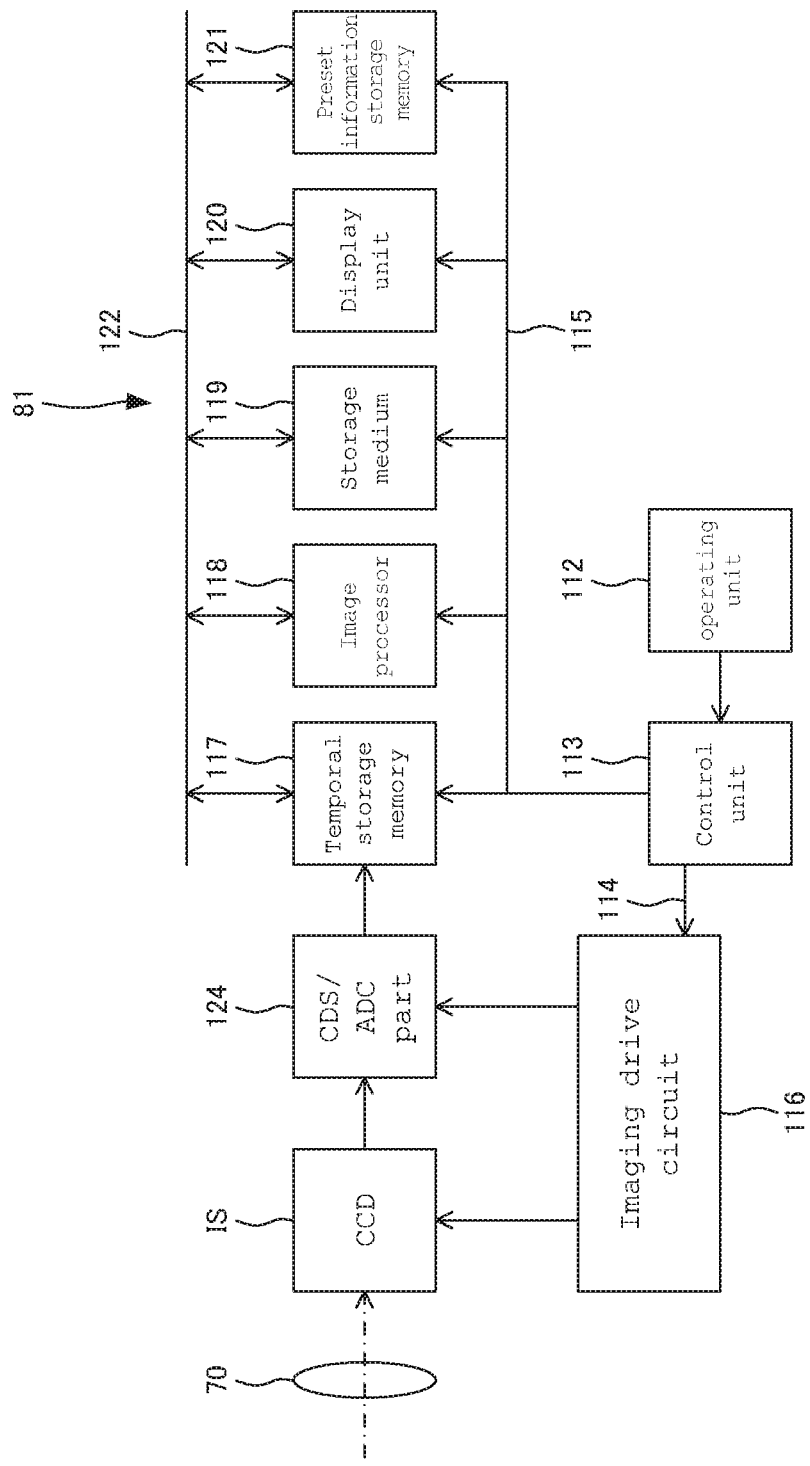
FIG. 25 is a block diagram for the internal circuitry of a main part of the digital camera according to one embodiment of the invention.

FIG. 25 is a block diagram for the internal circuitry of a main part of the digital camera 80 according to the embodiment described herein. Note here that in what follows, the processing means is made up of, for instance, a CDS/ADC 124, a temporal storage memory 117, and an image processor 118, and a storage means is made up of a memory medium and such.

As can be seen from FIG. 25, the digital camera 81 includes an operating unit 112, a control unit 113 connected to the operating unit 112, an imaging drive circuit 116/temporal storage memory 117 connected to the control signal output port of the control unit 113 by way of buses 114 and 115, an image processor 118, a memory medium 119, a display unit 120 and a preset information storage memory 121.

The abovementioned temporal storage memory 117, image processor 118, storage medium 119, display unit 120 and preset information storage memory 121 are designed such that data are mutually entered and produced out by way of a bus 122, and the imaging drive circuit 116 is connected with the imaging device IS and CDS/ADC 124.

The operating unit 112 includes various input buttons or switches, and event information entered from outside (by the camera operator) by way of them is notified to the control unit 113. The control unit 113 is typically a central processing unit (CPU) or the like, and includes a program memory (not shown) inside so that the digital camera 81 is controlled on its entirety according to the program stored in the program memory.

The imaging device IS such as CCD is driven and controlled by the imaging drive circuit 116 to convert the quantity of light per pixel of an object image formed via the optical unit 70 into an electric signal that is then produced out to the CDS/ADC 124.

The CDS/ADC 124 is a circuit in which the electric signal entered through the imaging device IS is amplified and subjected to analog-to-digital conversion to produce the image raw data (Bayer data hereinafter called the RAW data) subjected to only amplification/digital conversion processing out to the temporal storage memory 117.

The temporal storage memory 117 is a buffer comprising an SDRAM as an example or a memory device adapted to temporarily store the RAW data produced out from the CDS/ADC 124. The image processor 118 is a circuit adapted to read out the RAW data stored in the temporal storage memory 117 or the RWA data stored in the storage medium 119 thereby electrically implementing a variety of image processing including distortion correction based on image quality parameters designated by the control unit 113.

The storage medium 119 includes a detachably mounted card or stick type storage medium comprising flash memories as an example, and the RAW data transferred from the temporal storage memory 117 or the image data processed by the image processor 118 are recorded and retained in these flash memories.

The display unit 120 is made up of a liquid crystal display monitor or the like so as to display the taken RAW data, image date, operation menus, etc. The preset information storage memory 121 includes a ROM having a variety of image quality parameters stored beforehand, and a RAM adapted to store image quality parameters read out from the ROM by the input operation of the operating unit 112.

The digital camera 81 assembled in this way, because of incorporating the optical unit 70 according to the embodiment described herein, ensures that the imaging apparatus 80 is of smaller size and well compatible with the taking of moving images.

Figure 26:
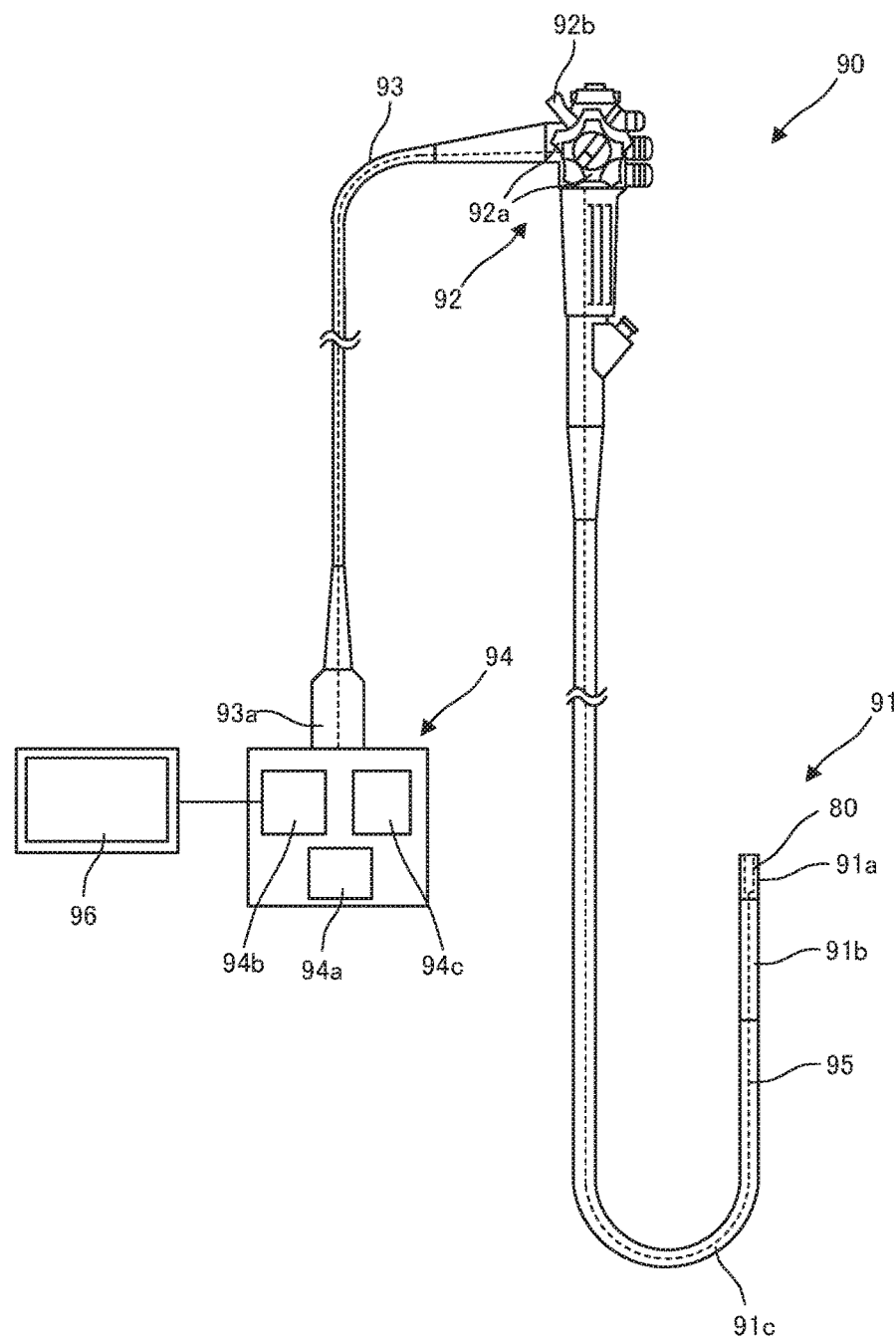
FIG. 26 is illustrative of one example of the endoscope including the imaging apparatus according to one embodiment of the invention.

FIG. 26 is illustrative of one example of the endoscope 90 including the imaging apparatus 80 according to the embodiment described herein.

The endoscope 90 according to the embodiment described herein is capable of insertion through a subject of interest such as the human body for optical taking of a given site of interest in the subject. Note here that the subject through which the endoscope 90 is to be inserted may be living bodies inclusive of the human body as well as artifacts such as machinery and buildings.

The endoscope 90 includes an insert part 91 inserted through the interior of the subject, an operating unit 92 positioned at the distal end of the insert part 91 and a universal cable 93 that is a composite cable let out from the operating unit 92.

The insert part 91 includes a distal-end portion 91a attached to the distal end, a bendable portion 91b located on the proximal end side of the distal-end portion 91a and a flexible tubular portion 91c located on the proximal end side of the bendable portion 91b and connected to the distal end side of the operating unit 92. The distal-end portion 91a has the imaging apparatus 80 (shown in FIG. 23) built inside. Note here that the endoscope 90 used may be a hard one having no flexible tubular portion 91c in the insert part 91.

The operating unit 92 includes an angle operating portion 92a for operation of the bending state of the bendable portion 91b and a zoom operating portion 92b for giving an instruction to the voice coil motor 10 (shown in FIG. 23) to implement zoom operation. The angle operating portion 92a has a knob form and the zoom operating portion 92b has a lever form; however, they may each be configured as a volume switch, a push switch or the like.

The universal cord 93 is a member for connecting the operating unit 92 to external hardware 94 by way of a connector 93a. The external hardware 94 includes a driving control portion 94a for controlling the bending state of the bendable portion 91b, an image control portion 94b for controlling the imaging apparatus 80, a light source control portion 94c for controlling a light source (not shown), and the like.

A cable 95 such as a wire, an electric wire, an optical fiber or the like is run through the insert part 91, operating unit 92 and universal cord 93. The wire is provided so as to connect the driving control portion 94a located in the external hardware 94 to the operating unit 92 and bendable portion 91b. The electric wire is provided for electric connections between the imaging apparatus 80 and the operating unit 92 and image control portion 94b. The optical fiber is provided for optical connections between the light source and the operating unit 92 and light source control portion 94c.

The driving control portion 94a is built up of an actuator or the like to move the wire advanceably/retractably for control of the bending state of the bendable portion 91b. The image control portion 94b implements driving control of the voice coil motor 10 built in the imaging apparatus 80 shown in FIG. 23 and processing of images taken through the imaging device IS. The images processed by the image control portion 94b appear on an image display unit 96. The light source control portion 94c is provided so as to control the brightness of light exiting out from the distal-end portion 91a, and so on.

It is here to be appreciated that the operating unit 92 and external hardware 94 may be formed separately from the insert part 91 for remote operation and control of the insert part 91.

The endoscope 90 assembled in this way, because of incorporating the imaging apparatus 80 according to the embodiment described herein, ensures that the imaging apparatus 80 is of smaller size and well compatible with quick zoom change and the taking of moving images.

Thus, one embodiment of the invention provides a drive unit including a tubular fixed portion 2 with a given axis C as center, a tubular movable part 3 located inside of the fixed part 2 and having the axis C as center, and a voice coil motor 10 capable of moving the movable part 3 relatively with respect to the fixed part 2 in the axis C direction by a coil 11 located in the fixed part 2 and a magnet 12 located in the movable part 3, wherein: in a state where the magnet is placed in the movable part 3, a first distance L1 from the axis C to the diametrically outer surface of the magnet 12 is longer than a second distance L2 from the axis C to the inner circumference surface of the fixed part 2. It is thus possible to reduce the diameter of the fixed part 2 and, hence, the size and weight of the drive unit 1. This ensures that the driving efficiency of the drive unit 1 is boosted up enough to provide rapid movement of the movable part 3.

In one embodiment of the drive unit 1 according to the invention, the fixed part 2 is provided with lightened portions 2a and 3a in positions corresponding to the diametrically outer surface 121 of the magnet 12. It is thus possible to reduce the size and weight of the drive unit 1 with recourse to simple structure.

In one embodiment of the drive unit 1 according to the invention, the step portion 34 comprising a plane orthogonal to the diametrical direction is formed on the outer circumference surface of the movable part 3, and the magnet 12 is located on the step portion 34. It is thus possible to locate the magnet 12 in a stable way and, hence, create a stable magnetic field thereby ensuring unerring movement of the movable part 3 to the fixed part 2.

In one embodiment of the drive unit 1 according to the invention, the movable part 3 includes the sliding surface 32a in abutment on the inner circumference surface 23 of the fixed part 2. It is thus possible to move the movable part 3 to the fixed part 2 while they are in constant contact with each other so that any tilting of the movable part 3 to the fixed part 2 can be prevented for unerring movement of the movable part 3.

In one embodiment of the drive unit 1 according to the invention, the diametrically outer surface of the magnet 12 is similar in shape to the inner circumference surface of the coil 11 in opposition to the diametrically outer surface of the magnet 12. It is thus possible to boost up the driving force of the drive unit 1.

In one embodiment of the drive unit 1 according to the invention, the coil 11 is wound along the outer circumference surface of the fixed part 2, and a portion of the coil 11 corresponding to the diametrically outer surface 121 of the magnet 12 conforms in shape to the diametrically outer surface 121 of the magnet 12. It is thus possible to boost up the driving force of the drive unit 1.

In one embodiment of the drive unit 1 according to the invention, the diametrically outer surface of the magnet is a plane. It is thus possible to set up the drive unit 1 easily.

In one embodiment of the drive unit 1 according to the invention, the magnet 12 includes an annular portion 122 along the outer surface of the movable part 3. It is thus possible to set up the drive unit 1 easily and make the placement of the magnet more stable so much so that there is a stable magnetic field created, leading to unerring movement of the movable part 3 to the fixed part 2.

In one embodiment of the drive unit 1 according to the invention, the magnet 12 comprises a first magnet 12a and a second magnet 12b adjacent to each other in the axial direction, the first magnet 12a and the second magnet 12b are diametrically magnetized with magnetic poles in opposite directions, and the coil 11 comprises a first coil 11a in opposition to the first magnet 12a and a second coil 11b in opposition to the second magnet 12b. It is thus possible to boost up the driving force of the drive unit 1.

In one embodiment of the optical unit 70 according to the invention, the movable part 3 includes the optical member Lv. Thus, the movement of the movable part 3 to the fixed part 2 permits for movement of the focal position of the optical unit 70.

In one embodiment of the imaging apparatus 80 according to the invention, it comprises the imaging device IS on which light passing through the optical member is incident, and the optical unit optical unit 70. It is thus possible to reduce the size and weight of the imaging apparatus 80. Further, the movement of the movable part 3 to the fixed part 2 permits for rapid zoom change of the imaging apparatus 80.

In one embodiment of the endoscope 90 according to the invention, it comprises the insert part 91 inserted through the interior of the body, and the imaging apparatus 80 located in the insert part 91. Thus, the endoscope 90 is of smaller size and capable of rapid zoom change well compatible with the taking of moving images.

It is here to be appreciated that the invention is in no sense limited to such embodiments as described. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Drive unit
2: Fixed part
23: Inner circumference surface
3: Movable part
10: Voice coil motor
11: Coil
12: Magnet
121: Diametrically outer surface

The invention claimed is:

1. A drive unit comprising:
a tubular fixed part with a central axis as center,
a tubular movable part located inside of the fixed part and having the central axis as center, and
a voice coil motor capable of moving the movable part relatively with respect to the fixed part in an axial direction, the voice coil motor including a coil located on an outer circumferential surface of the fixed part and a magnet located in the movable part,
wherein:
the fixed part is provided with a hole in a position corresponding to a diametrically outer surface of the magnet,
a part of the magnet is located in the hole,
in a state where the magnet is placed in the movable part, a first distance from the central axis to the diametrically outer surface of the magnet is longer than a second distance from the central axis to an inner circumferential surface of the fixed part;
a step portion comprising a plane orthogonal to a diametrical direction is formed on an outer circumference surface of the movable part, and
the magnet is located on the step portion.

2. An optical unit comprising:
the drive unit according to claim 1; and
an optical member configured to be movable with the movable part.

3. An imaging apparatus, comprising:
the drive unit according to claim 1;
an optical member configured to be movable with the movable part; and
an imaging device on which light passing through the optical member is incident.

4. An endoscope comprising:
an insert part configured to be inserted through an interior of a body;
the drive unit according to claim 1, the drive unit being disposed in the insert part;
an optical member configured to be movable with the movable part; and
an imaging device on which light passing through the optical member is incident.

5. A drive unit comprising:
a tubular fixed part with a central axis as center,
a tubular movable part located inside of the fixed part and having the central axis as center, and
a voice coil motor capable of moving the movable part relatively with respect to the fixed part in an axial direction, the voice coil motor including a coil located on an outer circumferential surface of the fixed part and a magnet located in the movable part,
wherein:
the fixed part is provided with a hole in a position corresponding to a diametrically outer surface of the magnet,
a part of the magnet is located in the hole,
in a state where the magnet is placed in the movable part, a first distance from the central axis to the diametrically outer surface of the magnet is longer than a second distance from the central axis to an inner circumferential surface of the fixed part; and the diametrically outer surface of the magnet is a plane.

6. An optical unit comprising:

the drive unit according to claim 5; and an optical member configured to be movable with the movable part.

7. An imaging apparatus, comprising:

the drive unit according to claim 5;

an optical member configured to be movable with the movable part; and an imaging device on which light passing through the optical member is incident.

8. An endoscope comprising:

an insert part configured to be inserted through an interior of a body;

the drive unit according to claim 5, the drive unit being disposed in the insert part;

an optical member configured to be movable with the movable part; and an imaging device on which light passing through the optical member is incident.

* * * * *